(12) United States Patent
Cremer et al.

(10) Patent No.: US 7,794,509 B2
(45) Date of Patent: Sep. 14, 2010

(54) TRICATIONIC DYES

(75) Inventors: Christian Cremer, Lörrach (DE); Olof Wallquist, Bottmingen (CH); Victor Paul Eliu, Lörrach (DE); Kishor Ramachandra Nivalkar, Mumbai (IN)

(73) Assignee: Ciba Corporation, Tarrytown, NY (US)

( * ) Notice: Subject to any disclaimer, the term of this patent is extended or adjusted under 35 U.S.C. 154(b) by 0 days.

(21) Appl. No.: 12/308,042

(22) PCT Filed: Jun. 4, 2007

(86) PCT No.: PCT/EP2007/055442

§ 371 (c)(1),
(2), (4) Date: May 15, 2009

(87) PCT Pub. No.: WO2007/144280

PCT Pub. Date: Dec. 21, 2007

(65) Prior Publication Data

US 2010/0011518 A1 Jan. 21, 2010

(30) Foreign Application Priority Data

Jun. 13, 2006 (IN) .................. 1019/CHE/2006

(51) Int. Cl.
*A61Q 5/10* (2006.01)
*C09B 29/00* (2006.01)

(52) U.S. Cl. .................. 8/405; 8/426; 8/437; 8/454; 8/463; 8/565; 8/568; 8/570; 8/573; 8/575; 534/778

(58) Field of Classification Search .................. 8/405, 8/426, 437, 454, 463, 565, 588, 570, 573, 8/575; 534/778

See application file for complete search history.

(56) References Cited

U.S. PATENT DOCUMENTS

| 5,125,930 A | 6/1992 | Taniguchi ............... 8/655 |
| 2004/0244127 A1 | 12/2004 | Adam et al. ............... 8/406 |
| 2006/0021162 A1* | 2/2006 | Greaves et al. ............. 8/406 |

FOREIGN PATENT DOCUMENTS

EP 1219683 7/2002

OTHER PUBLICATIONS

STIC Seach Report dated Feb. 3, 2010.*
English language abstract of EP 1219683, Jul. 3, 2002.

* cited by examiner

*Primary Examiner*—Eisa B Elhilo
(74) *Attorney, Agent, or Firm*—Mervin G. Wood

(57) ABSTRACT

Disclosed are tricationic dye compounds, useful for dyeing hair, wool, leather, silk, cellulose or polyamides. The dye compounds are of formula (1), where the groups are as defined in the specification and claims.

$$[D-E_1=E_2-K]^{3+}(An_1^-)(An_2^-)(An_3^-) \quad (1)$$

26 Claims, No Drawings

TRICATIONIC DYES

The present invention relates to novel tricationic dyes and compositions comprising these compounds, to a process for their preparation and to their use for dyeing of organic materials, such as keratin-containing fibers, wool, leather, silk, cellulose or polyamides, especially keratin-containing fibers, cotton or nylon, more preferably human hair.

Accordingly, the present invention relates to compounds of formula

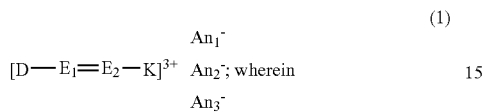

(1)

D is an aromatic or a cationic heteroaromatic group, which is optionally substituted by one or more than one $C_1$-$C_{14}$alkyl, $C_1$-$C_{14}$alkoxy, hydroxy-$C_1$-$C_{14}$alkyl, $C_3$-$C_8$cycloalkyl, —CN, $NO_2$, —$NR_3R_4$, halogen, $C_6$-$C_{10}$aryl, which is optionally substituted or $C_1$-$C_{14}$alkyl, or by one or more groups Z;

$E_1$ and $E_2$ independently from each other are =CH; or =N—;

K is an aromatic or heteroaromatic group which is optionally substituted by one or more than one $C_1$-$C_{14}$alkyl, $C_1$-$C_{14}$alkoxy, $C_3$-$C_8$cycloalkyl, $C_6$-$C_{10}$aryl, halogen, hydroxy, $NO_2$, —$NR_3R_4$, —$N(R_3)(CO)R_4$, —$SO_2NR_3R_4$, —$SONR_3R_4$ or by one or more Z; or a radical of formula —$NR_1R_2$;

$R_1$ and $R_2$ independently from each other are hydrogen; $C_1$-$C_{14}$alkyl; cyclo-$C_1$-$C_{14}$alkyl; $C_6$-$C_{10}$aryl; an aromatic or heteroaromatic group which is optionally substituted by one or more than one $C_1$-$C_{14}$alkyl, $C_1$-$C_{14}$alkoxy, $C_3$-$C_8$cycloalkyl, $C_6$-$C_{10}$aryl, halogen, hydroxy, —$NR_5R_6$, —$N(R_5)$—$(CO)R_5$ or by Z;

Z is a group of the formula (1a) *—$X_1$—$Y_1$—$W_1$, wherein $X_1$ is the direct bond; —$NR_7$—; —O—; —$NR_7(C=O)$—; —(CO)$NR_7$—; —O(C=O)—; —(CO)O—; or —(C=O)—;

$Y_1$ is the direct bond; $C_1$-$C_{12}$alkylene, which is optionally interrupted by —O—, —$NR_8$, —S—, —(C=O)—, —O(C=O)—, (C=O)O—, —$NR_7(C=O)$—, —(C=O)$NR_7$—, and which may substituted by $C_1$-$C_{14}$alkyl, hydroxy-$C_1$-$C_{14}$alkyl, hydroxy, —$NR_9R_{10}$ or halogen; or $C_6$-$C_{10}$arylene, which may substituted by $C_1$-$C_{14}$alkyl, hydroxy-$C_1$-$C_{14}$alkyl, hydroxy, amino or halogen;

$W_1$ is a cationic group; and $R_3$, $R_4$, $R_5$, $R_6$, $R_7$, $R_8$, $R_9$ and $R_{10}$ independently from each other are hydrogen; $C_1$-$C_{14}$alkyl; or Z; and $An_1^-$, $An_2^-$ and $An_3^-$ independently from each other are an anion.

$C_1$-$C_{14}$alkyl are straight chain or branched alkyl radicals like methyl, ethyl, n-propyl, isopropyl, n-butyl, sek.butyl, tert.butyl, amyl, isoamyl or tert.amyl, hexyl, 2-ethylhexyl, heptyl, octyl, isooctyl, nonyl, decyl, undecyl, dodecyl or tetradecyl.

$C_1$-$C_{14}$alkoxy is for example, methoxy, ethoxy, propoxy, isopropoxy, n-butoxy, sec-butoxy or tert-butoxy, amyl, isoamyl or tert.amyloxy, hexyloxy, 2-ethylhexyloxy, heptyloxy, octyloxy, isooctyloxy, nonyloxy, decyloxy, undecyloxy, dodecyloxy or tetradecyloxy.

$C_3$-$C_8$cycloalkyl is for example cyclopropyl, cyclobutyl, cyclopentyl, cycloheptyl, cyclooctyl or preferably cyclohexyl.

$C_6$-$C_{10}$aryl is for example naphthyl or phenyl, which are optionally substituted by one or more hydroxy, amino, halogen or $C_1$-$C_5$alkyl.

$C_1$-$C_5$alkylene is for example methylene, ethylene, propylene, butylene or pentylene which are optionally substituted by one or more hydroxy, amino, halogen or $C_1$-$C_5$alkyl.

Halogen is for example, fluoro, chloro, bromo or iodo, especially chloro and fluoro.

Preferably the compounds of formula (1) are selected from the compounds of the formulas

(2)

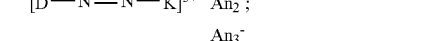

(3)

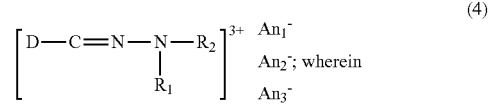

(4)

D, K, $R_1$, $R_2$, $An_1^-$, $An_2^-$ and $An_3^-$ are defined as in formula (1).

Preferred are compounds of formula (1) wherein D is selected from the radicals of formula (1b)

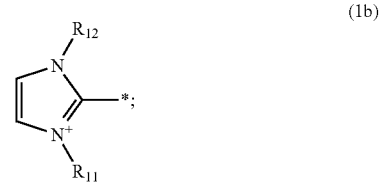

(1b)

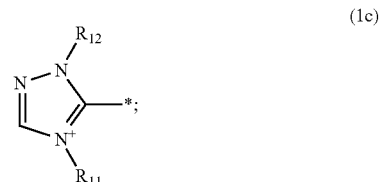

(1c)

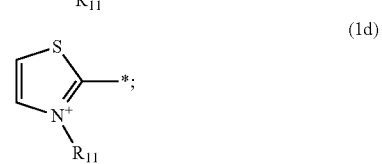

(1d)

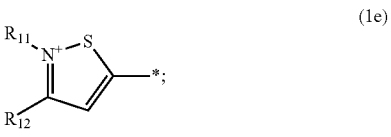

(1e)

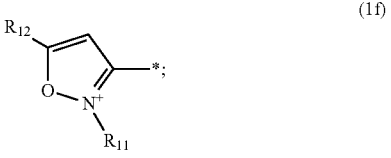

(1f)

-continued

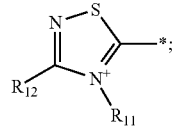 (1g)

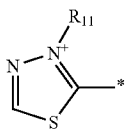 (1h)

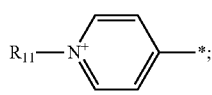 (1i)

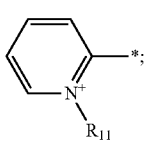 (1k)

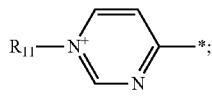 (1l)

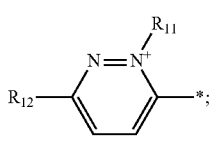 (1m)

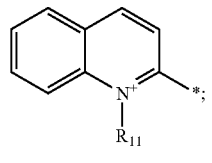 (1n)

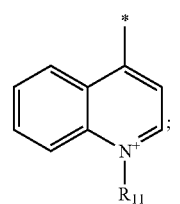 (1o)

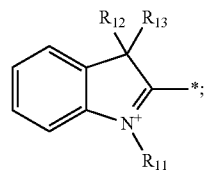 (1p)

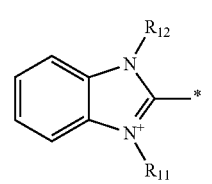 (1q)

-continued

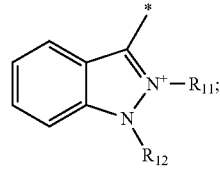

(1r)

(1s)

(1t)

(1u)

$R_{11}$ is unsubstituted or OH—, $C_1$-$C_{14}$alkoxy-, halogen-CN— or $NR_{14}R_{15}$— substituted $C_1$-$C_{14}$alkyl; or Z;

$R_{12}$ and $R_{13}$ independently from each other are hydrogen; or unsubstituted or OH—, $C_1$-$C_{14}$alkoxy-, halogen-, CN—, $NR_{16}R_{17}$— substituted $C_1$-$C_{14}$alkyl; $C_1$-$C_{14}$alkoxy; or Z;

$R_{14}$, $R_{15}$, $R_{16}$ and $R_{17}$ independently from each other are hydrogen; or $C_1$-$C_{14}$alkyl; and Z is defined as in formula (1).

More preferred are compounds of formula (1), wherein

K is phenyl or naphtyl, which may be substituted by $C_1$-$C_{14}$alkyl, $C_1$-$C_{14}$alkoxy, $C_3$-$C_8$cycloalkyl, $C_6$-$C_{10}$aryl, halogen, hydroxy, —$NR_3R_4$, —$N(R_3)$—$(CO)R_4$; or by one or more groups Z; wherein $R_3$, $R_4$, and Z are defined as in formula (1).

Preferably in formula (1)

Z is ($C_1$-$C_5$alkylene)-$W_1$; wherein

"$C_1$-$C_5$alkylene" may be interrupted by —O— or —$NR_8$— or substituted by OH; and $W_1$ and $R_8$ are defined as formula (1).

Preferably in formula (1)

$W_1$ is an aliphatic ammonium group or a cationic heteroaromatic group; and more preferably $W_1$ is selected from

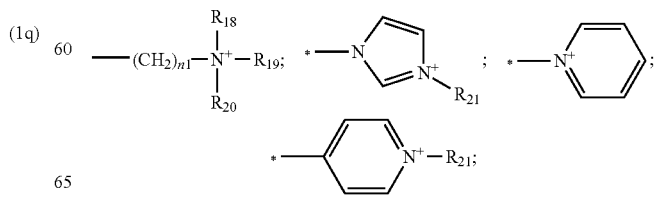

and

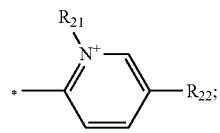

wherein
$R_{18}$, $R_{19}$, $R_{20}$, $R_{21}$ and $R_{22}$ are hydrogen; or $C_1$-$C_{14}$alkyl; and n1 is a number from 0 to 4.

More preferably in formula (1)
Z is selected from the radicals of formulas

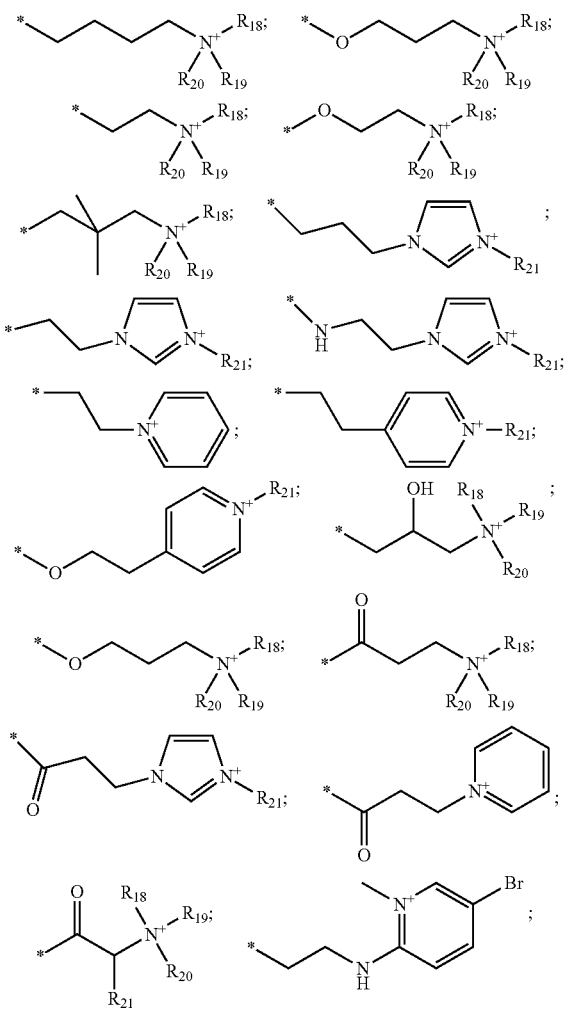

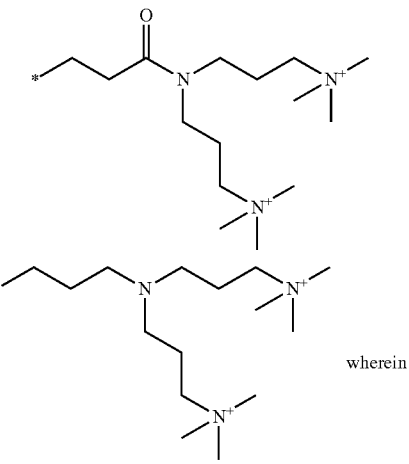

$R_{18}$, $R_{19}$, $R_{20}$ and $R_{21}$ are defined as above.
More preferred are compounds of formulae

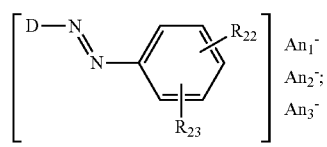
(5)

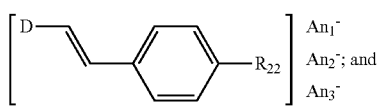
(6)

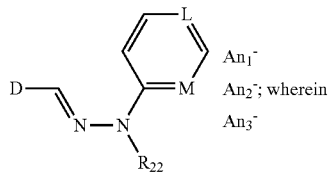
(7)

$R_{22}$ and $R_{23}$ independently from each other are *—$X_1$—$Y_1$—$W_1$;
L and M, independently from each other are —C=; or —$N^+(R_{24})$=;
$R_{24}$ is hydrogen; or $C_1$-$C_{14}$alkyl; and
D, $X_1$, $Y_1$ and W are defined as in formula (1).

Most preferred are compounds of formulae

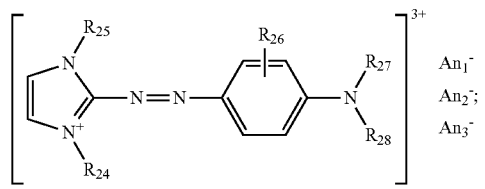
(8)

-continued

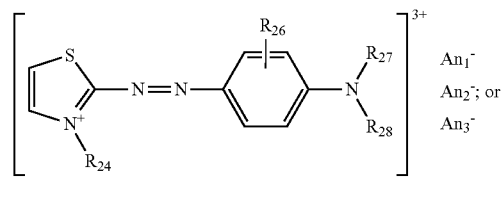
(9)

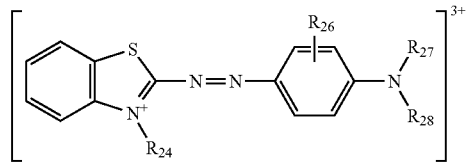
(10)

$R_{24}$, $R_{25}$, $R_{26}$, $R_{27}$ and $R_{28}$ independently from each other are hydrogen; $C_1$-$C_5$alkyl; hydroxy-$C_1$-$C_5$alkyl; hydroxy; halogen; $C_4$-$C_6$cycloalkyl; $C_6$-$C_{10}$aryl optionally containing heteroatoms; or Z; and $A_1^-$, $A_2^-$ and $A_3^-$ and Z are defined as in formula (1);

with the proviso that 2 radicals represent Z in order to obtain an overall charge of $3^+$.

Most preferred are also compounds of formulae

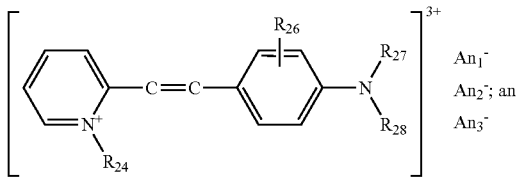
(11)

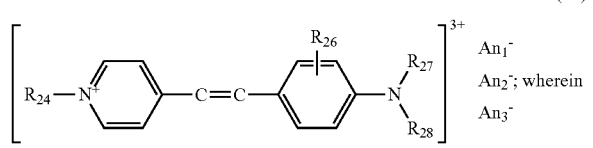
(12)

$R_{24}$, $R_{26}$, $R_{27}$ and $R_{28}$ independently from each other are hydrogen; $C_1$-$C_5$alkyl; hydroxy-$C_1$-$C_5$alkyl; hydroxy; halogen; $C_4$-$C_6$cycloalkyl; $C_6$-$C_{10}$aryl optionally containing heteroatoms; or Z; and Z and $A_1^-$, $A_2^-$ and $A_3^-$ are defined as in formula (1);

with the proviso that 2 radicals represent Z in order to obtain an overall charge of $3^+$.

Most preferred are also compounds of formulae

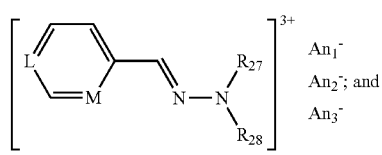
(13)

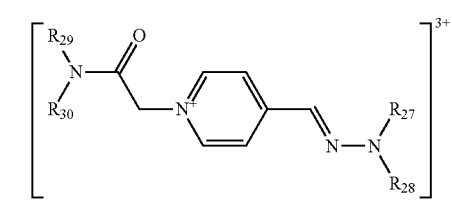
(14)

L and M independently from each other are —C═; or —N$^+$($R_{24}$)═;

$R_{27}$, $R_{28}$, $R_{29}$ and $R_{30}$ independently from each other are hydrogen; $C_1$-$C_{14}$alkyl; hydroxy-$C_1$-$C_{14}$alkyl; hydroxy; halogen; cyclo-$C_3$-$C_8$alkyl; or $C_6$-$C_{10}$aryl, which optionally contains hetero atoms; or a group Z;

$R_{24}$ is defined as in formula (8); and $A_1^-$, $A_2^-$ and $A_3^-$ and Z are defined as in formula (1);

with the proviso that 2 radicals represent Z in order to obtain an overall charge of $3^+$.

The present invention relates also to a process for the preparation of the dyes of formula (1).

A preferred method of preparing tricationic azo dyes is:

a) the reaction of a compound of formula

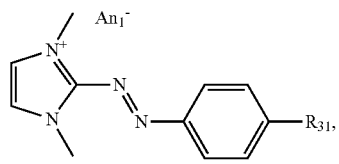
(16)

wherein $R_{31}$ is $C_1$-$C_6$alkoxy, or halide, preferred halides are chloride or fluoride, and $An_1^-$ is an anion, which is obtained according to methods known, such as described in Deligeorgiev et al., Dyes and Pigments, Vol. 31(3), pages 219-224, 1996, with a secondary amine of formula

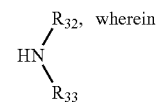
(17)

$R_{32}$ and $R_{33}$ are $C_1$-$C_5$ alkyl substituted with hydroxy, halogen especially chloro, or with tertiary amino groups, b) then, if $R_{32}$ and $R_{33}$ are substituted with tertiary amino groups, quaternization of the amino groups with an alkylating agent; or, if $R_{32}$ and $R_{33}$ are substituted with chloro, reaction with a tertiary amine or a quaternizable aromatic amine; or, if $R_{32}$ and $R_{33}$ are substituted with hydroxy groups, first conversion of the hydroxy groups into leaving groups for nucleophilic displacement by generally known procedures, and then reaction with a tertiary amine or a quaternizable aromatic amine.

Another preferred way of preparing tricationic azo dyes is:

a) the diazotization of a heterocyclic amine, especially one of the following:

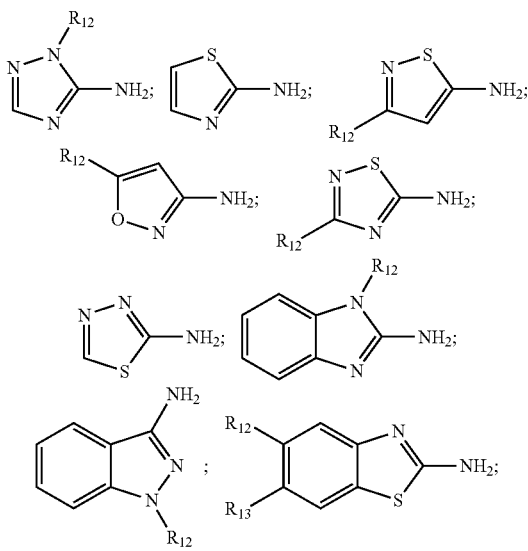

wherein the R groups have the same meaning as described above, b) then coupling of the diazotized amine with an aromatic compound, especially phenyl or naphtyl, which can be substituted by halogen, hydroxy or —$NR_{32}R_{33}$, in which $R_{32}$, $R_{33}$ is $C_1$-$C_5$ alkyl substituted with hydroxy, halogen especially chloro or with amino groups, c) then, if $R_{32}$, $R_{33}$ are substituted with amino groups, quaternization of the amino groups and the heterocycle with an alkylating agent; or, if $R_{32}$, $R_{33}$ are substituted by halogen, reaction with a tertiary amine or a quaternizable aromatic amine; or, if $R_{32}$, $R_{33}$ are substituted by hydroxy, first conversion of the hydroxy groups into a leaving groups for nucleophilic displacement by generally known procedures, and then reaction with a tertiary amine or a quaternizable aromatic amine, d) if the heterocycle was not already alkylated in step c) reaction with an alkylating agent.

A preferred method of preparing tricationic hydrazone dyes is:

a) the reaction of a compound of formula

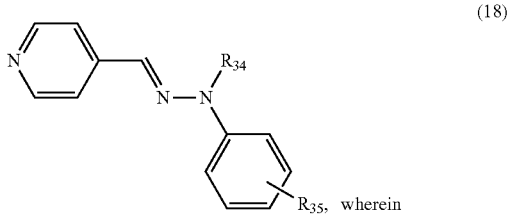

(18)

$R_{34}$ is hydrogen; $C_1$-$C_{14}$alkyl; cyclo-$C_3$-$C_8$alkyl; $C_6$-$C_{10}$aryl; $R_{35}$ is $C_1$-$C_{14}$alkyl, $C_1$-$C_{14}$alkoxy, $C_3$-$C_8$cycloalkyl, $C_6$-$C_{10}$aryl, halogen, hydroxy, amino, which can be prepared by a process described in patent WO 03/060015, p. 3 to 13, with an excess of a dihalide, especially dibromide, so that one reactive site of the dihalide remains unreacted, b) then reaction of the second reactive site of the dihalide with a secondary amine of Formula (17), c) then if $R_{32}$ and $R_{33}$ are substituted with amino groups, quaternization of the amino groups with an alkylating agent; or if $R_{32}$ and $R_{33}$ are substituted with chloro, reaction with a tertiary amine or a quaternizable aromatic amine; or, if $R_{32}$ and $R_{33}$ are substituted with hydroxy groups, first conversion of the hydroxy groups into leaving groups for nucleophilic displacement by generally known procedures, and then reaction with a tertiary amine or a quaternizable aromatic amine.

Another preferred way of preparing tricationic hydrazone dyes is a) acylation of a secondary amine of formula (17) with an acid chloride of the formula $M_1$-$CH_2$—CO-$M_2$, wherein $M_1$ and $M_2$ are independent from each other bromo or chloro, b) then reaction with the hydrazone of formula (18), c) then if $R_{32}$ and $R_{33}$ are substituted with tertiary amino groups, quaternization of the amino groups with an alkylating agent; or, if $R_{32}$ and $R_{33}$ are substituted with chloro, reaction with a tertiary amine or a quaternizable aromatic amine.

A preferred way for the preparation of tricationic styryl dyes is:

a) N-alkylation of α- or χ-picolin with an excess of a dihalide, especially dibromide, so that one reactive site of the dihalide remains unreacted, b) then reaction of the second reactive site of the dihalide with a secondary amine of formula (17), c) then condensation of the quaternized picolin with an aromatic aldehyde, d) then if $R_{32}$, $R_{33}$ are substituted with tertiary amino groups, quaternization of the amino groups with an alkylating agent; or, if $R_{32}$ and $R_{33}$ are substituted with chloro, reaction with a tertiary amine or a quaternizable aromatic amine; or, if $R_{32}$ and $R_{33}$ are substituted with hydroxy groups, first conversion of the hydroxy groups into leaving groups for nucleophilic displacement by generally known procedures, and then reaction with a tertiary amine or a quaternizable aromatic amine.

Another preferred way for the preparation of tricationic styryl dyes is:

a) acylation of a secondary amine of formula (17) with an acid chloride of the formula $M_1$-$CH_2$—CO-$M_2$, wherein $M_1$ and $M_2$ are independent from each other bromo or chloro, b) then reaction with α- or χ-picolin, c) then condensation off the methyl group of the picolin moiety with an aromatic aldehydes, d) then if $R_{32}$, $R_{33}$ are substituted with tertiary amino groups, quaternization of the amino groups with an alkylating agent; or, if $R_{32}$ and $R_{33}$ are substituted with chloro, reaction with a tertiary amine or a quaternizable aromatic amine.

In the processes mentioned above preferred:

alkylating agents are dimethyl sulfate, diethyl sulfate, methyl iodide, benzyl chloride, alkyl bromides and alkyl chlorides, tertiary amines are trimethyl amine, triethylamine and preferred aromatic amines are pyridine, pyrazine, pyrimidine and N-methylimidazole, leaving groups are tosylate, mesylate, sulfate, benzoylate, triflate, acetate, chloride, bromide or iodide.

The reaction is generally initiated by contacting; for example by mixing together the starting compounds or by drop wise addition of one starting compound to the other.

Customary, the temperature is in the range from 273 to 300 K, preferably from 290 to 300 K during the mixing of the starting compounds.

The reaction time is generally dependent on the reactivity of the starting compounds, on the selected reaction temperature and on the desired conversion. The selected duration of reaction is usually in the range from one hour to three days.

The reaction temperature is preferably in the range from 263 to 423K, especially in the range from 273 to 393K.

The reaction pressure is generally in the range from 70 kPa to 10 MPa, especially from 90 kPa to 5 MPa, and is more especially atmospheric pressure.

It may by desirable to conduct the reaction of compounds in the presence of a catalyst.

The molar ratio of compound of formula (1a) to the catalyst is generally selected in the range from 10:1 to 1:5, especially in the range from 10:1 to 1:1.

Suitable catalysts are for example an alkali metal $C_1$-$C_6$alkyloxide, such as sodium-, potassium or lithium $C_1$-$C_6$alkyloxide, preferably sodium methoxide, potassium methoxide or lithium methoxide, or sodium ethoxide, potassium ethoxide or lithium ethoxide; or tertiary amines, for example, such as quinuclidine, N-methylpiperidine, pyridine, trimethylamine, triethylamine, trioctylamine, 1,4-diazabicyclo[2.2.2]octan, quinuclidine, N-methylpiperidine; or alkali metal acetate, for example such as sodium acetate, potassium acetate, or lithium acetate.

Preferred are potassium acetate, sodium methoxide, pyridine and 1,4-diazabicyclo[2.2.2]octan.

In addition, the reactions can be carried out with or without solvent, but is preferably carried out in a solvent. Preference is given to organic solvents or solvent mixtures.

Within the context of this invention, solvents are organic solvents and water, or a mixture of organic solvents or a mixture of organic solvents and water.

Organic solvents are, for example, protic or aprotic polar organic solvents, such as alcohols, for example methanol, ethanol, n-propanol, isopropanol, butanol or glycols, especially isopropanol, or nitrile, such as acetonitrile or propionitrile, or amide, such as dimethylformamide, dimethylacetamide or N-methylpyridine, N-methylpyrrolidone, or sulfoxide, such as dimethyl-sulfoxide, or mixtures thereof.

The prepared product may be advantageously worked up and isolated, and if desired be purified.

Customary, the work up starts by decreasing the temperature of the reaction mixture in the range from 280 to 300 K, especially in the range from 290 to 300 K.

It may be of advantageous to decrease the temperature slowly, over a period of several hours.

In general, the reaction product is usually filtered and then washed with water or a salt solution and subsequently dried.

Filtration is normally carried out in standard filtering equipment, for example Büchner funnels, filter presses, pressurized suction filters, preferably in vacuo.

The temperature for the drying is dependent on the pressure applied. Drying is usually carried out in vacuo at 50-200 mbar.

The drying is usually carried out at a temperature in the range from 313 to 363 K, especially from 323 to 353 K, and more especially in the range from 328 to 348 K.

It has proved advantageous for the product to be purified by recrystallization after it has been isolated.

Organic solvents and solvent mixtures are suitable for the recrystallization. Preference is given to alcohols, for example methanol, ethanol, 2-propanol or butanol, especially 2-propanol.

To improve the solubility of the product it has been proved advantageous to exchange the counterions by generally known methods.

The dyes of formula (1) according to the invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties to washing, such as, for example, fastness to light, shampooing and rubbing.

Generally, hair dyeing agents on a synthetic base may be classified into three groups:

temporary dyeing agents
semipermanent dyeing agents, and
permanent dyeing agents.

The multiplicity of shades of the dyes can be increased by combination with other dyes.

Therefore the dyes of formula (1) of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The dyes of formula (1) may be used in combination with at least one single direct dye different from the dyes of formula (1).

Direct dyes do not require any addition of an oxidizing agent to develop their dyeing effect. Accordingly the dyeing results are less permanent than those obtained with permanent dyeing compositions. Direct dyes are therefore preferably used for semipermanent hair dyeings.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

More preferred direct dyes which are useful for the combination with at least one single dye of formula (1), especially for semi permanent dyeing, are:

2-amino-3-nitrophenol, 2-amino-4-hydroxyethylamino-anisole sulfate, 2-amino-6-chloro-4-nitrophenol, 2-chloro-5-nitro-N-hydroxyethylene-p-phenylendiamine, 2-hydroxyethyl-picramic acid, 2,6-diamino-3-((pyridine-3yl)-azo) pyridine, 2-nitro-5-glyceryl-methylanil, 3-methylamino-4-nitro-phenoxyethanol, 4-amino-2-nitrodiphenyleneamine-2'-carboxylic acid, 6-nitro-1,2,3,4-tetrahydroquinoxal, 4-N-ethyl-1,4-bis(2'-hydroxyethylamino-2-nitrobenzene hydrochloride, 1-methyl-3-nitro-4-(2'-hydroxyethyl)-aminobenzene, 3-nitro-p-hydroxyethylaminophenol, 4-amino-3-nitrophenol, 4-hydroxypropylamine-3-nitrophenol, hydroxyanthrylaminopropylmethyl morphlino methosulfate, 4-nitrophenyl-aminoethylurea, 6-nitro-p-toluidine, Acid Blue 62, Acid Blue 9, Acid Red 35, Acid Red 87 (Eosin), Acid Violet 43, Acid Yellow 1, Basic Blue 3, Basic Blue 6, Basic Blue 7, Basic Blue 9, Basic Blue 12, Basic Blue 26, Basic Blue 99, Basic Brown 16, Basic Brown 17, Basic Red 2, Basic Red 22, Basic Red 76, Basic Violet 14, Basic Yellow 57, Basic Yellow 9, Disperse Blue 3, Disperse Orange 3, Disperse Red 17, Disperse Violet 1, Disperse Violet 4, Disperse Black 9, Fast Green FCF, HC Blue 2, HC Blue 7, HC Blue 8, HC Blue 12, HC Orange 1, HC Orange 2, HC Red 1, HC Red 10-11, HC Red 13, HC Red 16, HC Red 3, HC Red BN, HC Red 7, HC Violet 1, HC Violet 2, HC Yellow 2, HC Yellow 5, HC Yellow 5, HC Yellow 6, HC Yellow 7, HC Yellow 9, HC Yellow 12, HC Red 8, hydroxyethyl-2-nitro-p-toluidine, N,N-Bis-(2-Hydroxyethyl)-2-nitro-p-phenylendiamine, HC Violet BS, Picramic Acid, Solvent Green 7.

Furthermore, the dyes of formula (1) may be combined with at least one cationic azo dye, for example the compounds disclosed in GB-A-2 319 776 as well as the oxazine dyes described in DE-A-299 12 327 and mixtures thereof with the other direct dyes mentioned therein, and even more preferred with cationic dyes such as Basic Yellow 87, Basic Orange 31 or Basic Red 51, or with cationic dyes as described in WO 01/66646, especially example 4, or with cationic dyes as described in WO 02/31056, especially example 6, the compound of formula 106; or the cationic dye of formula (3) as described in EP-A-714,954, or with a yellow cationic dye of formula

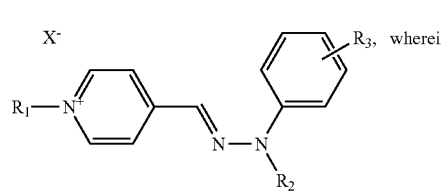

(DD1)

$R_1$ and $R_2$ are each independently of the other a $C_1$-$C_8$alkyl; or an unsubstituted or substituted benzyl;

$R_3$ is hydrogen; $C_1$-$C_8$alkyl; $C_1$-$C_8$alkoxy; cyanide; or halide; preferably hydrogen; and $X^-$ is an anion; and preferably a compound of formula (DD1), wherein $R_1$ is methyl; $R_2$ is benzyl; $R_3$ is hydrogen; and $X^-$ is an anion; or wherein $R_1$ is benzyl; $R_2$ is benzyl; $R_3$ is hydrogen; and $X^-$ is an anion; or wherein $R_1$ is benzyl; $R_2$ is methyl; $R_3$ is hydrogen; and $X^-$ is an anion.

Furthermore, cationic nitroaniline and anthraquinone dyes are useful for a combination with a dye of formula (1) for example the dyes as described in the following patent specifications: U.S. Pat. No. 5,298,029, especially in col 2, I. 33 to col 5, I. 38; U.S. Pat. No. 5,360,930, especially in col 2, I. 38 to col 5, I. 49; U.S. Pat. No. 5,169,403, especially in col 2, I. 30 to col 5, I. 38; U.S. Pat. No. 5,256,823, especially in col 4, I. 23 to col 5, I. 15; U.S. Pat. No. 5,135,543, especially in col 4, I. 24 to col 5, I. 16; EP-A-818 193, especially on p. 2, I. 40 to p. 3, I. 26; U.S. Pat. No. 5,486,629, especially in col 2, I. 34 to col 5, I. 29; and EP-A-758 547, especially on p. 7, I. 48 to p. 8, I. 19.

The dyes of formula (1) may also be combined with acid dyes, for example the dyes which are known from the international names (Color index), or trade names.

Preferred acid dyes which are useful for the combination with a dye of formula (1) are described in U.S. Pat. No. 6,248,314. They include Red Color No. 120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No. 104, Red Color No. 105(1), Red Color No. 106, Green Color No. 2, Green Color No. 3, Orange Color No. 207, Yellow Color No. 202(1), Yellow Color No. 202(2), Blue Color No. 202, Blue Color No. 203, Blue Color No. 205, Blue Color No. 2, Yellow Color No. 203, Blue Color No. 201, Green Color No. 201, Blue Color NO. 1, Red Color No. 230(1), Red Color No. 231, Red Color No. 232, Green Color No. 204, Green Color No. 205, Red Color No. 401, Yellow Color No. 403(1), Green Color No. 401, Green Color No. 402, Black Color No. 401 and Purple Color No. 401, especially Black Color No. 401, Purple Color 401, Orange Color No. 205.

These acid dyes may be used either as single component or in any combination thereof. Hair dye compositions comprising an acid dye are known. They are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 253 and 254.

Hair dye compositions which comprise an acid dye have a pH of 2-6, preferably 2-5, more preferably 2.5-4.0.

The dyes of formula (1) according to the present invention may also readily be used in combination with acid dyes and/or adjuvants, for example acid dyes and an alkylene carbonate, as described in U.S. Pat. No. 6,248,314, especially in examples 1 and 2;

acid hair dye compositions comprising various kinds of organic solvents represented by benzyl alcohol as a penetrant solvent have good penetrability into hair, as described in Japanese Patent Application Laid-Open Nos. 210023/1986 and 101841/1995;

acid hair dye compositions with a water-soluble polymer or the like to prevent the drooping of the hair dye composition, as described for example in Japanese Patent Application Laid-Open Nos. 87450/1998, 255540/1997 and 245348/1996;

acid hair dye compositions with a water-soluble polymer of aromatic alcohols, lower alkylene carbonates, or the like as described in Japanese Patent Application Laid-Open No. 53970/1998 and Japanese Patent Invention No. 23911/1973.

The dyes of formula (1) may also be combined with uncharged dyes, for example selected from the group of the nitroanilines, nitrophenylenediamines, nitroaminophenols, anthraquinones, indophenols, phenazines, phenothiazines, bispyrazolons, bispyrazol aza derivatives and methines.

Furthermore, the dyes of formula (1) may also be used in combination with oxidation dye systems.

Oxidation dyes, which, in the initial state, are not dyes but dye precursors are classified according to their chemical properties into developer and coupler compounds.

Suitable oxidation dyes are described for example in

DE 19 959 479, especially in col 2, I. 6 to col 3, I. 11;

"Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes);

Preferred developer compounds are for example primary aromatic amines, which are substituted in the para- or orthoposition with a substituted or unsubstituted hydroxy- or amino residue, or diaminopyridine derivatives, heterocyclic hydrazones, 4-aminopyrazol derivatives, 2,4,5,6-tetraminopyrimidine derivatives, or unsaturated aldehydes as described in DE 19 717 224, especially on p. 2, I. 50 to I. 66 and on p. 3 I. 8 to I. 12, or cationic developer compounds as described in WO 00/43367, especially on p., 2 I. 27 to p. 8, I. 24, in particular on p. 9, I. 22 to p. 11, I. 6.

Furthermore, developer compounds in their physiological compatible acid addition salt form, such as hydrochloride or sulfate can be used. Developer compounds, which have aromatic OH radicals are also suitable in their salt form together with a base, such as alkali metal-phenolates.

Preferred developer compounds are disclosed in DE 19959479, p. 2, l. 8-29.

More preferred developer compounds are p-phenylendiamine, p-toluoylendiamine, p-, m-o-aminophenol, N,N-bis-(2-hydroxyethyl)-p-phenylenediamine sulfate, 2-amino-4-hydroxyethylaminoanisole sulfate, hydroxyethyl-3,4-methylenedioxyanil, 1-(2'-hydroxyethyl)-2,5-diaminobenzene, 2,6-dimethoxy-3,5-diamino-pyridine, hydroxypropyl-bis-(N-hydroxyethyl-p-phenylenediamine) hydrochloride, hydroxyethyl-p-phenylenediamine sulfate, 4-amino-3-methylphenol, 4-methylaminophenol sulfate, 2-aminomethyl-4-aminophenol, 4,5-diamino-1-(2-hydroxyethyl)-1H-pyrazol, 4-amino-m-cresol, 6-amino-m-cresol, 5-amino-6-chloro-cresol, 2,4,5,6-tetraminopyrimidine, 2-hydroxy-4,5,6-triaminopyrimidine or 4-hydroxy-2,5,6-triaminopyrimidine sulfate.

Preferred coupler compounds are m-phenylendiamine derivatives, naphthole, resorcine and resorcine derivatives, pyrazolone and m-aminophenol derivatives, and most preferably the coupler compounds disclosed in DE 19959479, p. 1, l. 33 to p. 3, l. 11.

The dyes of formula (1) may also be used together with unsaturated aldehydes as disclosed in DE 19 717 224 (p. 2, l. 50 to l. 66 and on p. 3 l. 8 to l. 12) which may be used as direct dyes or, alternatively together with oxidation dye precursors.

Further preferred for a combination with a dye of formula (1) are the following oxidation dye precursors:

the developer/-coupler combination 2,4,5,6-tetraminopyrimidine and 2-methylresorcine for assessing of red shades;

p-toluenediamine and 4-amino-2-hydroxytoluene for assessing of blue-violet shades;

p-toluenediamine and 2-amino-4-hydroxyethylaminoanisole for assessing of blue shades;

p-toluenediamine and 2,4-diamino-phenoxyethynol for assessing of blue shades;

methyl-4-aminophenol and 4-amino-2-hydroxytoluene for assessing of orange shades;

p-toluenediamine and resorcine for assessing of brown-green shades;

p-toluenediamine and 1-naphthol for assessing of blue-violet shades, or p-toluenediamine and 2-methylresorcine for assessing of brown-gold shades.

Furthermore, autooxidizable compounds may be used in combination with the dyes of formula (1).

Autooxidizable compounds are aromatic compounds with more than two substituents in the aromatic ring, which have a very low redox potential and will therefore be oxidized when exposed to the air. The dyeings obtained with these compounds are very stable and resistant to shampoo.

Autooxidizable compounds are for example benzene, indol, or indol, especially 5,6-dihydroxyindol or 5,6-dihydroxyindol. derivatives as described in WO 99/20234, especially on p. 26, l. 10 to p. 28, l. 15, or in WO 00/28957 on p. 2, third paragraph.

Preferred autooxidizable benzene derivatives are 1,2,4-trihydroxybenzene, 1-methyl-2,4,5-trihydroxybenzene, 2,4-diamino-6-methylphenol, 2-amino-4-methylaminophenol, 2,5-diamino-4-methyl-phenol, 2,6-diamino-4-diethylaminophenol, 2,6-diamino-1,4-dihydroxybenzene, and the salts of these compounds, which are accessible with acid.

Preferred autooxidizable indol derivatives are 5,6-dihydroxyindol, 2-methyl-5,6-dihydroxyindol, 3-methyl-5,6-dihydroxyindole, 1-methyl-5,6-dihydroxyindol, 2,3-dimethyl-5,6-dihydroxyindol, 5-methoxy-6-dihydroxyindol, 5-acetoxy-6-hydroxyindol, 5,6-diacetoxyindol, acid of 5,6-dihydroxyindol-2-carbonacid, and the salts of these compounds, which are accessible with acid.

The dyes of formula (1) may also be used in combination with naturally occurring dyes, such as henna red, henna neutral, henna black, chamomile blossom, sandalwood, black tea, *Rhamnus frangula* bark, sage, campeche wood, madder root, catechu, sedre and alkanet root. Such dyeings are described, for example, in EP-A-404 868, especially on p. 3, l. 55 to p. 4, l. 9.

Furthermore, the dyes of formula (1) may also be used in combination with capped diazotised compounds.

Suitable diazotised compounds are for example the compounds of formulae (1)-(4) in WO 2004/019897 (bridging gages 1 and 2) and the corresponding watersoluble coupling components (I)-(IV) as disclosed in the same reference on p. 3 to 5.

Further preferred dyes or dye combinations which are useful for the combination with a dye of formula (1) according to the present invention are described in (DC-01): WO 95/01772, wherein mixtures of at least two cationic dyes are disclosed, especially p. 2, l. 7 to p. 4, l. 1, preferably p. 4, l. 35 to p. 8, l. 21; formulations p. 11, last §-p. 28, l. 19;

(DC-02): U.S. Pat. No. 6,843,256, wherein cationic dyes are disclosed, especially the compounds of formulae (1), (2), (3) and (4)(col. 1, l. 27-col. 3, l. 20, and preferably the compounds as prepared in the examples 1 to 4 (col. 10, l. 42 to col. 13, l. 37; formulations col. 13, l. 38 to col. 15, l. 8;

(DC-03): EP 970 685, wherein direct dyes are described, especially p. 2, l. 44 to p. 9, l. 56 and preferably p. 9, l. 58 to p. 48, l. 12; processes for dyeing of keratin-containing fibers especially p. 50, l. 15 to 43; formulations p. 50, l. 46 to p. 51, l. 40;

(DC-04): DE-A-19 713 698, wherein direct dyes are described, especially p. 2, l. 61 to p. 3, l. 43; formulations p. 5, l. 26 to 60;

(DC-05): U.S. Pat. No. 6,368,360, wherein directed dyes (col. 4, l. 1 to col. 6, l. 31) and oxidizing agents (col. 6, l. 37-39) are disclosed; formulations col. 7, l. 47 to col. 9, l. 4;

(DC-06): EP 1 166 752, wherein cationic dyes (p. 3, l. 22-p. 4, l. 15) and anionic UV-absorbers (p. 4, l. 27-30) are disclosed; formulations p. 7, l. 50-p. 9, l. 56;

(DC-07): EP 998,908, wherein oxidation dyeings comprising a cationic direct dye and pyrazolo-[1,5-a]-pyrimidines (p. 2, l. 48-p. 4, l. 1) are disclosed; dyeing formulations p. 47, l. 25 to p. 50, l. 29;

(DC-08): FR-2788432, wherein combinations of cationic dyes with Arianors are disclosed, especially p. 53, l. 1 to p. 63, l. 23, more especially p. 51 to 52, most especially Basic Brown 17, Basic brown 16, Basic Red 76 and Basic Red 118, and/or at least one Basic Yellow 57, and/or at least one Basic Blue 99; or combinations of arianoren and/or oxidative dyes, especially p. 2, l. 16 to p. 3, l. 16; dyeing formulations on p. 53, l. 1 to p. 63, l. 23;

(DC-09): DE-A-19 713 698, wherein the combinations of direct dyes and permanent-wave fixing comprising an oxidation agent, an oxidation dye and a direct dye are disclosed; especially p. 4, l. 65 to p. 5, l. 59;

(DC-10): EP 850 638, wherein developer compounds and oxidizing agents are disclosed; especially p. 2, l. 27 to p. 7, l. 46 and preferably p. 7, l. 20 to p. 9, l. 26; dyeing formulations p. 2, I. 3-12 and I. 30 to p. 14, and p. 28, I. 35-p. 30, I. 20; preferably p. 30, I. 25-p. 32, I. 30;

(DC-11): U.S. Pat. No. 6,190,421 wherein extemporaneous mixtures of a composition (A) containing one or more oxidation dye precursors and optionally one or more couplers, of a composition (B), in powder form, containing one or more direct dyes (col. 5, I. 40-col. 7, I. 14), optionally dispersed in an organic pulverulent excipient and/or a mineral pulverulent excipient, and a composition (C) containing one or more oxidizing agents are disclosed; formulations col. 8, I. 60-col. 9, I. 56;

(DC-12): U.S. Pat. No. 6,228,129, wherein a ready-to-use composition comprising at least one oxidation base, at least one cationic direct dye and at least one enzyme of the 2-electron oxidoreductase type in the presence of at least one donor for the said enzyme are disclosed; especially col. 8, I. 17-col. 13, I. 65; dyeing formulations in col. 2, I. 16 to col. 25, I. 55, a multi-compartment dyeing device is described in col. 26, I. 13-24;

(DC-13): WO 99/20235, wherein compositions of at least one cationic dye and at least one nitrated benzene dye with cationic direct dyes and nitro benzene direct dyes are described; on p. 2, I. 1 to p. 7, I. 9, and p. 39, I. 1 to p. 40 I. 11, preferably p. 8, I. 12 to p. 25 I. 6, p. 26, I. 7 to p. 30, I. 15; p. 1, I. 25 to p. 8, I. 5, p. 30, I. 17 to p. 34 I. 25, p. 8, I. 12 to p. 25 I. 6, p. 35, I. 21 to 27, especially on p. 36, I. 1 to p. 37;

(DC-14): WO 99/20234, wherein compositions comprising at least one direct cationic dye and at least one autooxidisable dye, especially benzene, indol and indol. derivatives are described, preferably direct dyes on p. 2, I. 19 to p. 26, I. 4, and autooxidisable dyes as disclosed especially on p. 26, I. 10 to p. 28, I. 15; dyeing formulations especially on p. 34, I. 5 to p. 35, Ii 18;

(DC-15): EP 850 636, wherein oxidation dyeing compositions comprising at least one direct dye and at least one meta-aminophenol derivative as coupler component and at least one developer compound and an oxidizing agent are disclosed, especially p. 5, I. 41 to p. 7, I. 52, dyeing formulations p. 19, I. 50-p. 22, I. 12;

(DC-16): EP-A-850 637, wherein oxidation dyeing compositions comprising at least one oxidation base selected from para-phenylenediamines and bis(phenyl)alkylenediamines, and the acid-addition salts thereof, at least one coupler selected from meta-diphenols, and the acid-addition salts thereof, at least one cationic direct dye, and at least one oxidizing agent are disclosed, especially p. 6, I. 50 to p. 8, I. 44 are disclosed; dyeing formulations p. 21, I. 30-p. 22, I. 57;

(DC-17): WO 99/48856, wherein oxidation dyeing compositions comprising cationic couplers are disclosed, especially p. 9, I. 16-p. 13, I. 8, and p. 11, I. 20-p. 12, I. 13; dyeing formulations p. 36, I. 7-p. 39, I. 24;

(DC-18): DE 197 172 24, wherein dyeing agents comprising unsaturated aldehydes and coupler compounds and primary and secondary amino group compounds, nitrogen-containing heterocyclic compounds, amino acids, oligopeptides, aromatic hydroxy compounds, and/or at least one CH-active compound are disclosed p. 3, I. 42-p. 5 I. 25; dyeing formulations p. 8, I. 25-p. 9, I. 61.

In the dye combinations disclosed in the references (DC-01-DC-18) above, the dyes of formula (1) according to the present invention may be added to the dye combinations or dyeing formulations or one or more of the dye components may be replaced with at least one dye of formula (1).

The present invention also relates to formulations, which are used for the dyeing of organic materials, preferably keratin-containing fibers, and most preferably human hair, comprising at least one dye of formula (1).

Preferably the dyes of formula (1) are incorporated into the composition for treating organic material, preferably for dyeing in amounts of 0.001-5% by weight (hereinafter indicated merely by "%"), particularly 0.005-4%, more particularly 0.2-3%, based on the total weight of the composition.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, I. 16 to 31.

The pH value of the ready-to-use dyeing compositions is usually from 2 to 11, preferably from 5 to 10.

One preferred embodiment of the present invention relates to the formulation of dyes, wherein the dyes of formula (1) are in powder form.

Powder formulations are preferably used if stability and/or solubility problems as for example described in DE 197 13 698, p. 2, I. 26 to 54 and p. 3, I. 51 to p. 4, I. 25, and p. 4, I. 41 to p. 5 I. 59.

Suitable cosmetic hair-care formulations are hair-treatment preparations, e.g. hair-washing preparations in the form of shampoos and conditioners, hair-care preparations, e.g. pre-treatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, I. 70 to col 3, I. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts; for example emulsifiers may be present in the dyeing compositions in concentrations from 0.5 to 30% by weight and thickeners in concentrations from 0.1 to 25% by weight of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, l. 1 to p. 244, l. 12.

If the dyes of formula (1) are used together with oxidation dyes and/or the addition salts thereof with an acid, they may be stored separately or together. Preferably the oxidation dyes and the direct dyes which are not stable to reduction are stored separately.

The dyes of formula (1) may be stored in a liquid to paste-like preparation (aqueous or non-aqueous) or in the form of a dry powder.

When the dyes are stored separately, the reactive components are intimately mixed with one another directly before use. In the case of dry storage, a defined amount of hot (from 50 to 80° C.) water is usually added and a homogeneous mixture prepared before use.

The dyeing compositions according to the invention may comprise any active ingredients, additives or adjuvants known for such preparations, like surfactants, solvents, bases, acids, perfumes, polymeric adjuvants, thickeners and light stabilisers.

The following adjuvants are preferably used in the hair dyeing compositions of the present invention:

- non-ionic polymers, for example vinylpyrrolidone/vinyl acrylate copolymers, polyvinylpyrrolidone and vinylpyrrolidone/vinyl acetate copolymers and polysiloxanes;
- cationic polymers, such as quaternised cellulose ethers, polysiloxanes having quaternary groups, dimethyldiallylammonium chloride polymers, copolymers of dimethyldiallylammonium chloride and acrylic acid, as available commercially under the name Merquat® 280 and the use thereof in hair dyeing as described, for example, in DE-A-4 421 031, especially p. 2, l. 20 to 49, or EP-A-953 334, especially p. 27, l. 17 to p. 30, l. 11;
- acrylamide/dimethyldiallylammonium chloride copolymers, diethyl-sulfate-quaternised dimethylaminoethyl methacrylate/vinylpyrrolidone copolymers, vinylpyrrolidone/imidazolinium methochloride copolymers;
- quaternised polyvinyl alcohol:
- zwitterionic and amphoteric polymers, such as acrylamido-propyltrimethylammonium chloride/acrylate copolymers and octylacrylamide/methyl methacrylate/tert-butyl-aminoethyl methacrylate/2-hydroxypropyl methacrylate copolymers;
- anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers;
- thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such amylose, amylopectin and dextrins, clays, e.g. bentonite or fully synthetic hydrocolloids such as, for example, polyvinyl alcohol;
- structuring agents, such as glucose and maleic acid;
- hair-conditioning compounds, such as phospholipids, for example soya lecithin, egg lecithin, cephalins, silicone oils, and conditioning compounds, such as those described in DE-A-19 729 080, especially p. 2, l. 20 to 49, EP-A-834 303, especially p. 2, l. 18-p. 3, l. 2, or EP-A-312 343, especially p. 2, l. 59-p. 3, l. 11;
- protein hydrolysates, especially elastin, collagen, keratin, milk protein, soya protein and wheat protein hydrolysates, condensation products thereof with fatty acids and also quaternised protein hydrolysates;
- perfume oils, dimethyl isosorbitol and cyclodextrins,
- solubilisers, such as ethanol, isopropanol, ethylene glycol, propylene glycol, glycerol and diethylene glycol,
- anti-dandruff active ingredients, such as piroctones, olamines and zinc Omadine,
- substances for adjusting the pH value;
- panthenol, pantothenic acid, allantoin, pyrrolidonecarboxylic acids and salts thereof, plant extracts and vitamins;
- cholesterol;
- light stabilisers and UV absorbers as listed in Table below:

TABLE 1

UV absorbers which may be use in the dyeing compositions of the present invention

| No. | Chemical Name | CAS No. |
| --- | --- | --- |
| 1 | (+/−)-1,7,7-trimethyl-3-[(4-methylphenyl)methylene]bicyclo-[2.2.1]heptan-2-one | 36861-47-9 |
| 2 | 1,7,7-trimethyl-3-(phenylmethylene)bicyclo[2.2.1]heptan-2-one | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2,2'-dihydroxy-4,4'-dimethoxybenzophenone | 131-54-4 |
| 8 | 2,2'-Dihydroxy-4-methoxybenzophenone | 131-53-3 |
| 9 | 1-[4-(1,1-dimethylethyl)phenyl]-3-(4-methoxyphenyl)propane-1,3-dione | 70356-09-1 |
| 10 | 3,3,5-Trimethyl cyclohexyl-2-hydroxy benzoate | 118-56-9 |
| 11 | Isopentyl p-methoxycinnamate | 71617-10-2 |
| 12 | Menthyl-o-aminobenzoate | 134-09-8 |
| 13 | Menthyl salicylate | 89-46-3 |
| 14 | 2-Ethylhexyl 2-cyano,3,3-diphenylacrylate | 6197-30-4 |
| 15 | 2-ethylhexyl 4-(dimethylamino)benzoate | 21245-02-3 |
| 16 | 2-ethylhexyl 4-methoxycinnamate | 5466-77-3 |
| 17 | 2-ethylhexyl salicylate | 118-60-5 |

TABLE 1-continued

UV absorbers which may be use in the dyeing compositions of the present invention

| No. | Chemical Name | CAS No. |
|---|---|---|
| 18 | Benzoic acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine | 88122-99-0 |
| 19 | Benzoic acid, 4-amino-, ethyl ester, polymer with oxirane | 113010-52-9 |
| 20 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 21 | Triethanolamine salicylate | 2174-16-5 |
| 22 | 2,2'-Methylene-bis-[6-(2H-benzotriazol-2-yl)-4-(1,1,3,3-tetramethyl-butyl)-phenol] | 103597-45-1 |
| 23 | 2,4-bis{[4-(2-ethylhexyloxy)-2-hydroxy]-phenyl}-6-(4-methoxyphenyl)-(1,3,5)-triazine (Tinosorb S) | 187393-00-6 |
| 24 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester | 154702-15-5 |
| 25 | Phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| 26 | Dimethicodiethylbezalmalonate | 207574-74-1 |
| 27 | Benzoic acid, 2-[4-(diethylamino)-2-hydroxybenzoyl]-, hexyl ester | 302776-68-7 |
| 28 | 1,3,5-Triazine, 2,4,6-tris(4-methoxyphenyl)- | 7753-12-0 |
| 29 | 1,3,5-Triazine, 2,4,6-tris[4-[(2-ethylhexyl)oxy]phenyl]- | 208114-14-1 |
| 30 | 2-Propenoic acid, 3-(1H-imidazol-4-yl)- | 104-98-3 |
| 31 | Benzoic acid, 2-hydroxy-, [4-(1-methylethyl)phenyl]methyl ester | 94134-93-7 |
| 32 | 1,2,3-Propanetriol, 1-(4-aminobenzoate) | 136-44-7 |
| 33 | Benzeneacetic acid, 3,4-dimethoxy-a-oxo- | 4732-70-1 |
| 34 | 2-Propenoic acid, 2-cyano-3,3-diphenyl-, ethyl ester | 5232-99-5 |
| 35 | Anthralinic acid, p-menth-3-yl ester | 134-09-8 |
| 36 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 37 | 2-Hydroxy-4-methoxy benzophenone-5-sulfonic acid | 4065-45-6 |
| 38 | Alpha-(2-oxoborn-3-ylidene)toluene-4-sulphonic acid and its salts | 56039-58-8 |
| 39 | Methyl N,N,N-trimethyl-4-[(4,7,7-trimethyl-3-oxobicyclo[2,2,1]hept-2-ylidene)methyl]anilinium sulphate; | 52793-97-2 |
| 40 | 4-aminobenzoic acid | 150-13-0 |
| 41 | 2-phenyl-1H-benzimidazole-5-sulphonic acid | 27503-81-7 |
| 42 | 3,3'-(1,4-phenylenedimethylene)bis[7,7-dimethyl-2-oxo-bicyclo[2.2.1]heptane-1-methanesulfonic acid] | 90457-82-2 |
| 43 | 1H-Benzimidazole-4,6-disulfonic acid, 2,2'-(1,4-phenylene)bis-, disodium salt | 180898-37-7 |
| 44 | Benzenesulfonic acid, 3-(2H-benzotriazol-2-yl)-4-hydroxy-5-(1-methylpropyl)-, monosodium salt | 92484-48-5 |
| 45 | 1-Dodecanaminium, N-[3-[[4-(dimethylamino)benzoyl]amino]-propyl]N,N-dimethyl-, salt with 4-methylbenzenesulfonic acid (1:1) | 156679-41-3 |
| 46 | 1-Propanaminium, N,N,N-trimethyl-3-[(1-oxo-3-phenyl-2-propenyl)-amino]-, chloride | 177190-98-6 |
| 47 | 1H-Benzimidazole-4,6-disulfonic acid, 2,2'-(1,4-phenylene)bis- | 170864-82-1 |
| 48 | 1-Propanaminium, 3-[[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 49 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |

The use of UV absorbers can effectively protect natural and dyed hair from the damaging rays of the sun and increase the wash fastness of dyed hair.

Furthermore, the following UV absorbers or combinations may be used in the dyeing compositions according to the invention:

cationic benzotriazole UV absorbers as for example described in WO 01/36396 especially on p. 1, I. 20 to p. 2, I. 24, and preferred on p. 3 to 5, and on p. 26 to 37;

cationic benzotriazole UV in combination with antioxidants as described in WO 01/36396, especially on p. 11, I. 14 to p. 18;

UV absorbers in combination with antioxidants as described in U.S. Pat. No. 5,922,310, especially in col 2, I. 1 to 3;

UV absorbers in combination with antioxidants as described in U.S. Pat. No. 4,786,493, especially in col 1, 42 to col 2, I. 7, and preferred in col 3, 43 to col 5, I. 20;

combination of UV absorbers as described in U.S. Pat. No. 5,830,441, especially in col 4, I. 53 to 56;

combination of UV absorbers as described in WO 01/36396, especially on p. 11, I. 9 to 13; or triazine derivatives as described in WO 98/22447, especially on p. 1, I. 23 to p. 2, I. 4, and preferred on p. 2, I. 11 to p. 3, I. 15 and most preferred on p. 6 to 7, and 12 to 16.

Suitable cosmetic preparations may usually contain from 0.05 to 40% by weight, preferably from 0.1 to 20% by weight, based on the total weight of the composition, of one or more UV absorbers.

consistency regulators, such as sugar esters, polyol esters or polyol alkyl ethers;

fats and waxes, such as spermaceti, beeswax, montan wax, paraffins, fatty alcohols and fatty acid esters;

fatty alkanolamides;

polyethylene glycols and polypropylene glycols having a molecular weight of from 150 to 50 000, for example such as those described in EP-A-801 942, especially p. 3, I. 44 to 55, complexing agents, such as EDTA, NTA and phosphonic acids, swelling and penetration substances, such as polyols and polyol ethers, as listed extensively, for example, in EP-A-962 219, especially p. 27, I. 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole;

opacifiers, such as latex;

pearlising agents, such as ethylene glycol mono- and distearate;

propellants, such as propane-butane mixtures, $N_2O$, dimethyl ether, $CO_2$ and air;

antioxidants;

sugar-containing polymers, as described in EP-A-970 687, especially p. 28, I. 17 to p. 29, I. 23;

quaternary ammonium salts, as described in WO 00/10517, especially p. 44, I. 16 to p. 46, I. 23.

Bacteria inhibiting agents, like preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations;

The dyeing compositions according to the present invention generally comprise at least one surfactant. Suitable surfactants are zwitterionic or ampholytic, or more preferably anionic, non-ionic and/or cationic surfactants.

Suitable anionic surfactants in the dyeing compositions according to the present invention include all anionic surface-active substances that are suitable for use on the human body. Such substances are characterised by an anionic group that imparts water solubility, for example a carboxylate, sulfate, sulfonate or phosphate group, and a lipophilic alkyl group having approximately 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanolammonium salts having 2 or 3 carbon atoms in the alkanol group:

linear fatty acids having 10 to 22 carbon atoms (soaps), ether carboxylic acids of formula R—O—$(CH_2$—$CH_2$—$O)_x$—$CH_2$—COOH, in which R is a l.ar alkyl group having 10 to 22 carbon atoms and x=0 or from 1 to 16, acyl sarcosides having 10 to 18 carbon atoms in the acyl group, acyl taurides having 10 to 18 carbon atoms in the acyl group, acyl isothionates having 10 to 18 carbon atoms in the acyl group, sulfosuccinic mono- and di-alkyl esters having 8 to 18 carbon atoms in the alkyl group and sulfosuccinic monoalkylpolyoxyethyl esters having 8 to 18 carbon atoms in the alkyl group and from 1 to 6 oxyethyl groups, linear alkane sulfonates having 12 to 18 carbon atoms, linear α-olefin sulfonates having 12 to 18 carbon atoms, α-sulfo fatty acid methyl esters of fatty acids having 12 to 18 carbon atoms, alkyl sulfates and alkyl polyglycol ether sulfates of formula R'—$O(CH_2$—$CH_2$—$O)_{x'}$—$SO_3H$, in which R' is a preferably l.ar alkyl group having 10 to 18 carbon atoms and x'=0 or from 1 to 12, mixtures of surface-active hydroxysulfonates according to DE-A-3 725 030, especially p. 3, I. 40 to 55, sulfated hydroxyalkylpolyethylene and/or hydroxyalkylenepropylene glycol ethers according to DE-A-3 723 354, especially p. 4, I. 42 to 62, sulfonates of unsaturated fatty acids having 12 to 24 carbon atoms and 1 to 6 double bonds according to DE-A-3 926 344, especially p. 2, I. 36 to 54, esters of tartaric acid and citric acid with alcohols which are addition products of approximately from 2 to 15 molecules of ethylene oxide and/or propylene oxide with fatty alcohols having from 8 to 22 carbon atoms, or anionic surfactants, as described in WO 00/10518, especially p. 45, I. 11 to p. 48, I. 3.

Preferred anionic surfactants are alkyl sulfates, alkyl polyglycol ether sulfates and ether carboxylic acids having 10 to 18 carbon atoms in the alkyl group and up to 12 glycol ether groups in the molecule, and also especially salts of saturated and especially unsaturated $C_8$-$C_{22}$carboxylic acids, such as oleic acid, stearic acid, isostearic acid and palmitic acid.

Surface-active compounds that carry at least one quaternary ammonium group and at least one —COO⁻ or —SO₃⁻ group in the molecule are terminated zwitterionic surfactants. Preference is given the so-called betaines, such as the N-alkylN,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazol. having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocoamidopropyl betaine.

Ampholytic surfactants are surface-active compounds that, in addition to a $C_8$-$C_{18}$-alkyl or -acyl group and contain at least one free amino group and at least one —COOH or —SO₃H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$-$C_{18}$acylsarcosine.

Suitable non-ionic surfactants are described in WO 00/10519, especially p. 45, I. 11 to p. 50, I. 12. Non-ionic surfactants contain as hydrophilic group, for example, a polyol group, a polyalkylene glycol ether group or a combination of polyol and polyglycol ether groups. Such compounds are, for example:

- addition products of 2 to 30 mol of ethylene oxide and/or 0 to 5 mol of propylene oxide with I.ar fatty alcohols having 8 to 22 carbon atoms, with fatty acids having 12 to 22 carbon atoms and with alkylphenols having 8 to 15 carbon atoms in the alkyl group,
- $C_{12}$-$C_{22}$ fatty acid mono- and di-esters of addition products of 1 to 30 mol of ethylene oxide with glycerol,
- $C_8$-$C_{22}$alkyl-mono- and -oligo-glycosides and ethoxylated analogues thereof,
- addition products of 5 to 60 mol of ethylene oxide with castor oil and hydrogenated castor oil,
- addition products of ethylene oxide with sorbitan fatty acid esters,
- addition products of ethylene oxide with fatty acid alkanolamides.

The surfactants which are addition products of ethylene and/or propylene oxide with fatty alcohols or derivatives of such addition products may either be products having a "normal" homologue distribution or products having a restricted homologue distribution. "Normal" homologue distribution are mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts.

The use of products having restricted homologue distribution may be preferred.

Examples of cationic surfactants that can be used in the dyeing compositions according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyldimethyl-lammonium chloride, lauryldimethylammonium chloride, lauryldimethylbenzylammonium chloride and tricetylmethylammonium chloride. Further cationic surfactants that can be used in accordance with the invention are quaternised protein hydrolysates.

Also suitable are cationic silicone oils, such as, for example, the commercially available products Q2-7224 (manufacturer: Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80), or silicones, as described in WO 00/12057, especially p. 45, I. 9 to p. 55, I. 2.

Alkylamidoamines, especially fatty acid amidoamines, such as the stearylamidopropyldimethylamine obtainable under the name Tego Amid® 18 are also preferred as surfactants in the present dyeing compositions. They are distinguished not only by a good conditioning action but also especially by their good biodegradability.

An example of a quaternary sugar derivative that can be used as cationic surfactant is the commercial product Glucquat® 100, according to CTFA nomenclature a "lauryl methyl gluceth-10 hydroxypropyl dimonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

A further embodiment of the present invention relates to the dyeing of keratin-containing fibers.

The processes comprises
(a) treating the keratin-containing fiber with at least one dye of formula (1), and
(b) leaving the fiber to stand and then rinsing the fiber.

The dyes of formula (1) are suitable for all-over dyeing of the hair, that is to say when dyeing the hair on a first occasion, and also for re-dyeing subsequently, or dyeing of locks or parts of the hair.

The dyes of formula (1) are applied on the hair for example by massage with the hand, a comb, a brush, or a bottle, or a bottle, which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with at least one dye of formula (1), a base and an oxidizing agent.

A preferred embodiment for dyeing keratin-containing fibers, in particular human hair, with a dye of formula (1) and an oxidizing agent, comprises $a_1$) treating the keratin-containing fiber with the oxidizing agent, which optionally contains at least one dye of formula (1), $b_1$) treating the keratin-containing fiber with an oxidizing agent free composition, which optionally contains at least one dye of formula (1); or alternatively $a_2$) treating the keratin-containing fiber with an oxidizing agent free composition, which optionally contains at least one dye of formula (1);

b$_2$) treating the keratin-containing fiber with an oxidizing agent, which optionally contains least one dye of formula (1), with the proviso that at least in one of the process steps a$_1$), a$_2$), b$_1$) or b$_2$) a dye of formula (1) is present.

In general, the oxidizing agent containing composition is left on the fiber for 0 to 15 minutes, in particular for 0 to 5 minutes at 15 to 45° C.

The oxidizing agent free composition usually comprises customary adjuvants and additives. Preferred are those, which are described in German Patent Application, in col 3, l. 17 to l. 41.

In general, the dye of formula (1) and the oxidizing agent free composition are left on the fiber for 5 to 45 minutes, in particular for 10 to 25 minutes at 15 to 50° C.

One preferred embodiment of the process is to wash the hair after dyeing with a shampoo and/or a weak acid, such as citric acid or tartrate acid.

The dyes of formula (1) which are stable to reduction can be stored together with the oxidizing agent free compositions and may be applied as a single composition.

Advantageously the compositions comprising a dye of formula (1) which are not stable to reduction are prepared with the oxidizing agent free composition just before the dyeing process.

In a further embodiment, the dye of formula (1) and the oxidizing agent free composition may be applied simultaneously or in succession.

Customary, the oxidizing agent containing composition is evenly applied in a sufficient amount related to the amount of hair, usually in amounts of 30 to 200 g.

Oxidizing agents are for example persulfate or dilute hydrogen peroxide solutions, hydrogen peroxide emulsions or hydrogen peroxide gels, alkal. earth metal peroxides, organic peroxides, such as urea peroxides, melamine peroxides, or alkalimetalbromat fixations are also applicable if a shading powder on the basis of semi-permanent, direct hair dyes is used.

Further preferred oxidizing agents are oxidizing agents to achieve lightened coloration, as described in WO 97/20545, especially p. 9, l. 5 to 9, oxidizing agents in the form of permanent-wave fixing solution, as described in DE-A-19 713 698, especially p. 4, l. 52 to 55, and l. 60 and 61 or EP-A-1062940, especially p. 6, l. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% by weight the corresponding composition.

The oxidizing agents may be present in the dyeing compositions according to the invention preferably in an amount from 0.01% to 6%, especially from 0.01% to 1%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

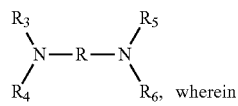

wherein

R is a propylene residue, which may be substituted with OH or $C_1$-$C_{14}$alkyl, $R_3$, $R_4$, $R_5$ and $R_6$ are independently or dependently from each other hydrogen, $C_1$-$C_{14}$alkyl or hydroxy-($C_1$-$C_{14}$)alkyl.

The pH-value of the oxidizing agent containing composition is usually about 2 to 7, and in particular about 2 to 5.

One preferred method of applying formulations-comprising the dyes of formula (1) on the keratin-containing fiber, preferably the hair is by using a multi-compartment dyeing device or "kit" or any other multi-compartment packaging system, as described for example in WO 97/20545 on p. 4, l. 19 to l. 27.

The first compartment contains for example at least one dye of formula (1) and optionally further direct dyes and a basifying agent, and in the second compartment an oxidizing agent; or in the first compartment at least one dye of formula (1) and optionally further direct dyes, in the second compartment a basifying agent and in the third compartment an oxidizing agent.

Preferably, a ready-to-use composition is prepared according to a first preferred embodiment by a process which comprises a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler, especially selected from meta-phenylenediamines and the acid-addition salts thereof, and at least one dye of formula (1), on the other hand, a composition (B) containing, in a medium which is suitable for dyeing, at least one oxidizing agent and mixing (A) and (B) together immediately before applying this mixture to the keratin-containing fibers.

According to a second preferred embodiment for the preparation of the ready-to-use dye composition, the process includes a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler compound, especially selected from meta-phenylenediamines and the acid-addition salts thereof; on the other hand, a composition (A') comprising, in a medium which is suitable for dyeing, at least one dye of formula (1), and finally, a composition (B) containing, in a medium which is suitable for dyeing, at least one oxidizing agent as defined above, and mixing them together at the time of use immediately before applying this mixture to the keratin-containing fibers.

The composition (A') used according to this second embodiment may optionally be in powder form, the cationic dye(s) of formula (1)(themselves) constituting, in this case, all of the composition (A') or optionally being dispersed in an organic and/or inorganic pulverulent excipient.

When present in the composition A', the organic excipient may be of synthetic or natural origin and is selected in particular from crosslinked and non-crosslinked synthetic polymers, polysaccharides such as celluloses and modified or unmodified starches, as well as natural products such as sawdust and plant gums (guar gum, carob gum, xanthan gum, etc.).

When present in the composition (A'), the inorganic excipient may contain metal oxides such as titanium oxides, aluminium oxides, kaolin, talc, silicates, mica and silicas.

An very suitable excipient in the dyeing compositions according to the invention is sawdust.

The powdered composition (A') may also contain binders or coating products in an amount which preferably does not exceed approximately 3% by weight relative to the total weight of composition (A'). These binders are preferably selected from oils and liquid fatty substances of inorganic, synthetic, animal or plant origin.

The composition (A') may optionally contain other adjuvants, in powdered form, in particular surfactants of any kind, hair conditioners such as, for example, cationic polymers, etc.

Generally the hair is rinsed after treatment with the dyeing solution and/or permanent-wave solution.

A further preferred embodiment of the present invention relates to a method of dyeing hair with oxidative dyes, which comprises a. mixing at least one dye of formula (1) and optionally at least one coupler compound and at least one developer compound, and an oxidizing agent, which optionally contains at least one further dye, and
b. contacting the keratin-containing fibers with the mixture as prepared in step a.

For adjusting the pH-value organic or inorganic acids, as for example described in DE 199 59 479, col 3, I. 46 to I. 53 are suitable.

Furthermore, the present invention relates to a process of dyeing of keratin-containing fibers of the dyes of formula (1) with autooxidable compounds and optionally further dyes.

The process comprises a. mixing at least one autooxidable compound and at least one developer compound and at least one dye of formula (1) and optionally further dyes, and
b. treating the keratin-containing fiber with the mixture prepared in step a.

Furthermore, the present invention relates to a process for dyeing keratin-containing fibers with the dyes of formula (1) and capped diazotised compounds, which comprises, a. treating the keratin-containing fibers under alkaline conditions with at least one capped diazotised compound and a coupler compound, and optionally a developer compound ad optionally an oxidizing agent, and optionally in the presence of a further dye, and optionally with at least one dye of formula (1); and
b. adjusting the pH in the range of 6 to 2 by treatment with an acid, optionally in the presence of a further dye, and optionally at least one dye of formula (1), with the proviso that at least in one step a. or b. at least one dye of formula (1) is present.

The capped diazotised compound and coupler compound and optionally the oxidizing agent and developer compound can be applied in any desired order successively or simultaneously.

Preferably, the capped diazotised compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotised compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkal. dyeing composition applied in the first stage to that of acid dyeing composition applied in the second stage is preferably about from 1:3 to 3:1, especially about 1:1.

The alkaline dyeing compositions of step a. and the acid dyeing compositions of step b. are left on the fiber for 5 to 60 minutes at 15 to 45° C., in particular for 5 to 45 minutes at 20 to 30° C.

Furthermore, the present invention relates to a process for dyeing keratin-containing fibers with the dyes of formula (1) and at least one acid dye.

The following examples serve to illustrate the processes for dyeing without limiting the processes thereto. Unless specified otherwise, parts and percentages relate to weight. The amounts of dye specified are relative to the material being dyed.

PREPARATION EXAMPLES

Example A1

Step 1: 86 g of 3,3'-bis(dimethylamino)-dipropylamine are added to a suspension of 23 g of the compound of formula

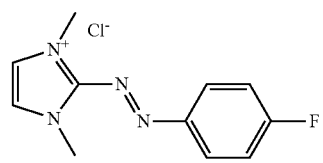

(101)

in 500 ml acetonitrile under stirring.

The reaction mass is heated to reflux for 4 h (the reaction is monitored by TLC). The acetonitrile is evaporated under reduced pressure and the resulting residue is stirred (triturated) under nitrogen with cold diethyl ether (500 ml) for 0.5 h.

Careful filtration under inert atmosphere is carried out with additional washings of cold diethyl ether (1000 ml).

The solid obtained is immediately transferred to a R. B. flask and dried under vacuum to get 33 g of a dark red solid.

Step 2: 20 g of this material is slowly added to 133 g dimethyl sulfate under stirring. During the addition the reaction mass is maintained at room temperature by external cooling. The reaction mixture is further stirred at room temperature for 16 h. Cold diethyl ether (200 ml) is added to the reaction mass and stirred for 2 h. Ether is decanted and the above step is repeated with cold diethyl ether (2×200 ml).

The reaction mass is allowed to settle by keeping in the refrigerator overnight.

It is filterated under nitrogen and the obtained solid is stirred for 2 h with chloroform (200 ml). Filtration followed by triturating with specially dried diethyl ether (2×200 ml) affords 30 g of a dark red solid of formula

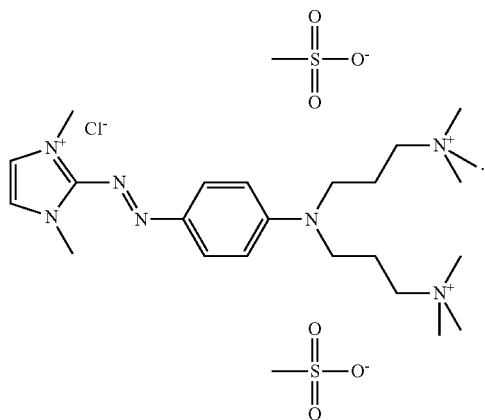

(102)

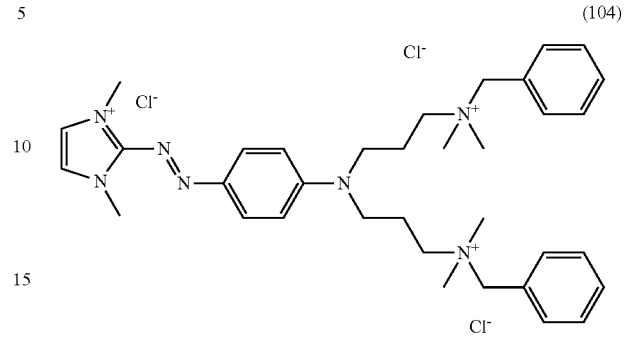

(104)

$^1$H NMR (CD$_3$OD, 400 MHz) δ 8.08 (d, 2H), 7.57 (s, 2H), 7.11 (d, 2H), 4.04 (s, 6H), 3.71 (t, 4H), 3.67 (s, 6H), 3.53 (t, 4H), 3.18 (s, 12H), 2.21 (p, 4H). UV/VIS (water): λ$_{max}$ 506 nm.

Example A2

The compound of formula (102)(1.5 g, 2.2 mmol) is dissolved in deionized water (20 ml) followed by addition of NaCl (0.28 g, 4.8 mmol) and KCl (0.36 g, 4.8 mmol).

The reaction mass is heated at 45-50° C. for 2 h. Water is evaporated under reduced pressure.

The residue is treated with absolute ethanol and filterated.

Solvent evaporation followed by trituration with ether (2×20 mL) gives 1.03 g of a dark red solid of formula

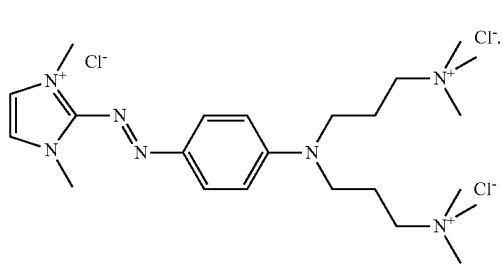

(103)

$^1$H NMR (CD$_3$OD, 400 MHz) δ 8.03 (m, 2H), 7.56 (s, 2H), 7.12 (m, 2H), 4.05 (s, 6H), 3.73 (t, 4H), 3.56 (m, 4H), 3.19 (s, 18H), 2.22 (m, 4H).

Example A3

The compound obtained in step 1 of example A1 (1.05 g, 2.5 mmol) is stirred at room temperature with benzyl chloride (3.165 g, 25 mmol) for 2 h.

The reaction mixture is vigorously stirred with diethyl ether (4×25 ml) and the ether layer is decanted.

Drying under vacuum afforded 1.36 g of a reddish violet dye of formula $^1$H NMR (CD$_3$OD, 400 MHz) δ 8.06 (m, 2H), 7.56 (m, 10H), 7.34 (m, 2H), 7.11 (m, 2H), 4.60 (s, 4H), 4.06 (s, 6H), 3.74 (m, 4H), 3.49 (m, 4H), 3.09 (s, 12H), 2.30 (m, 4H).

Example A4

Step 1: A mixture of conc. H$_2$SO$_4$ (57 ml) and water (47 ml) is introduced in a 500 ml 3-necked round bottom flask under external cooling.

2-amino-6-methoxybenzothiazole (22.2 g) is added slowly under vigorous stirring to this solution.

The white suspension is cooled to −7° C. The ice-cold solution of nitrosylsulfuric acid is then added over a period of 15 min maintaining the temperature in the range of −7 to −5° C.

The reaction mixture is further stirred for 4 hours at −5° C.

Urea (1.8 g) is added to the reaction mixture under stirring to decompose the traces of excess nitrous acid.

The cold diazo-solution is then poured onto to crushed ice (72 g) over a period of 5-10 min under mechanical stirring. Crushed ice (123 g) is added To this and the temperature is maintained at −5° C. N-phenyl diethanolamine (22.38 g) is added in portion over a period of 15 min under stirring to the above solution. The temperature is maintained at −5° C. by addition of ice (123 g) and stirring is continued for 15 min.

The stirring is stopped and reaction mixture kept at room temperature overnight (16 h). A sodium hydroxide (36%, ca. 200 ml) solution is added to the reaction mixture (which is cooled externally) till the pH reaches adjusts in the range of 3-4. The reaction mixture is then neutralized (pH 6 to 7) by addition of saturated solution of NaHCO$_3$.

The filtration of the solid followed by washings with water (100 ml×4) affords brown-red colored solid, which can be crystallized from methanol.

Step 2: A suspension of the compound obtained in the previous step (5.58 g) in dichloromethane (100 mL) is cooled to 0° C. TEA (6.81 g) is added to the above suspension under stirring. A solution of tosyl chloride (10.68 g) in dichloromethane (50 ml) is then added dropwise to the above suspension over a period of 30 min, keeping the temperature at 0° C. The reaction mixture is stirred overnight (16 h) at room temperature. The solvent is evaporated under reduced pressure and the residue is stirred with cold water (150 ml). The solid obtained is filtered and washed with water (2×100 mL).

Crystallization from a chloroform/methanol mixture (50 ml) [90:10 (v/v)] affords 7 g of a dark brownish red solid.

Step 3: A suspension of sodium hydride (50%)(0.345 g) in dry DMF (20 ml) is cooled down to 0° C. Imidazole (0.489 g) is then added and the reaction mass stirred for 10 min. The compound obtained in the previous step (2.04 g, 3 mmol) is added to the above suspension at 0° C. and the whole mass is stirred at 0° C. for 15 min.

The reaction mixture was warmed up to room temperature and stirring continued for 3 h (The progress of the reaction is monitored by TLC). The reaction mass is slowly poured onto cold water (50 ml). The solid is filterated off and chromatographed on silica gel (eluent, 95:5 (v/v) dichloromethane: methanol).

The product is obtained as a dark red compound (650 mg).

Step 4: The compound obtained in the previous step (0.4 g) is stirred with dimethyl sulfate (2.11 g) for 16 h. The reaction mixture is vigorously stirred (and decanted) with diethyl ether (4×25 ml). The solid is washed with chloroform:methanol (98:2) [100 ml] to furnish 0.53 g of a dark blue solid of the formula

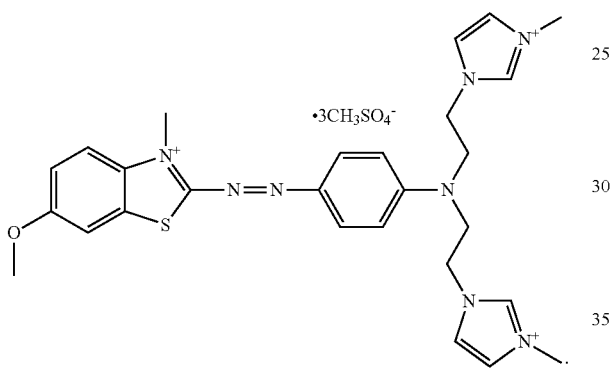
(105)

$^1$H NMR (CD$_3$OD, 400 MHz) δ=3.68 (s, 9H), 3.86 (s, 6H), 3.92 (s, 3H), 4.22 (t, 4H), 4.42 (s, 3H), 4.59 (t, 4H), 7.2 (d, J=9.2 Hz, 2H), 7.4 (dd, J=2.4 Hz, 1H), 7.57 (s, 2H), 7.7 (d, J=2.4 Hz, 1H), 7.74 (s, 2H), 8.03 (d, J=9.6 Hz, 1H), 8.11 (s, 2H), 9 (s, 2H). UV/VIS (water): λ$_{max}$ 592 nm.

Example A5

Step 1: The compound obtained in step 1 of example 4 (3.72 g) is heated with thionyl chloride (14.8 ml) at 55-60° C. for 30 min. The excess of thionyl chloride is removed under reduced pressure and the residue is basified with a saturated solution of NaHCO$_3$ (50 ml). The solid is filterated off and washed with water (2×50 ml).

The solid is purified by column chromatography (eluent, 75:25 chloroform:hexane) to furnish a dark red solid (2.45 g). EIMS m/z 409 [M]$^+$, Step 2: A mixture of the compound obtained in the previous step (0.818 g) and pyridine (5 ml) is heated at 100° C. for 3 h. After cooling to room temperature the reaction mixture is vigorously stirred (and decanted) with diethyl ether (2×15 ml).

Finally the solid is filterated off and washed with dichloromethane (50 ml) to afford 0.692 g of a dark red colour solid of formula

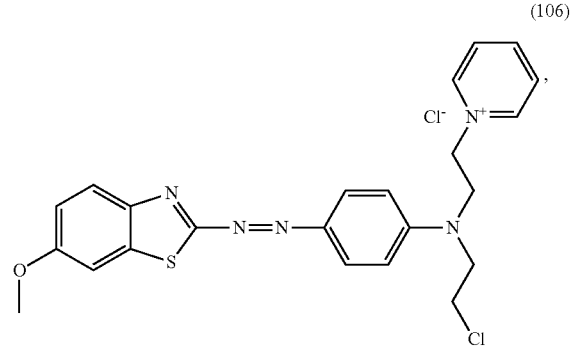
(106)

which can be used as such for dyeing hair.

Step 3: A mixture of the compound of formula (106) (0.5 g), pyridine (2 ml) and N-methyl-2-pyrrolidone (5 ml) is subjected to heating at 120° C. for 16 h.

After cooling to room temperature the reaction mixture is vigorously stirred (and decanted) with diethyl ether (2×15 ml).

Finally the solid is filterated off and washed with dichloromethane (50 ml) to give 0.498 g of a dark red colour solid of formula (107)

which can be used as such for dyeing hair.

$^1$H NMR (CD$_3$OD, 400 MHz) δ=3.85 (t, 3H), 4.25 (t, 4H), 4.9 (t, 4H), 6.93 (d, 2H), 7.15 (dd, J=2.4 Hz, 1H), 7.49 (d, J=2.4 Hz, 1H), 7.79 (d, J=9.6 Hz, 2H), 7.9 (d, J=8.8 Hz, 1H), 8.06 (m, 4H), 8.55 (t, J=8.0 Hz, 2H), 9.05 (d, J=5.6 Hz, 4H).

Step 4: The compound of formula (107) (0.19 g) is stirred with dimethyl sulfate (1.28 g) for 16 h.

The reaction mixture is vigorously stirred (and decanted) with diethyl ether (4×25 ml). The solid is washed with chloroform:methanol (98:2) [100 ml] to furnish 0.2 g of a dark blue solid of formula

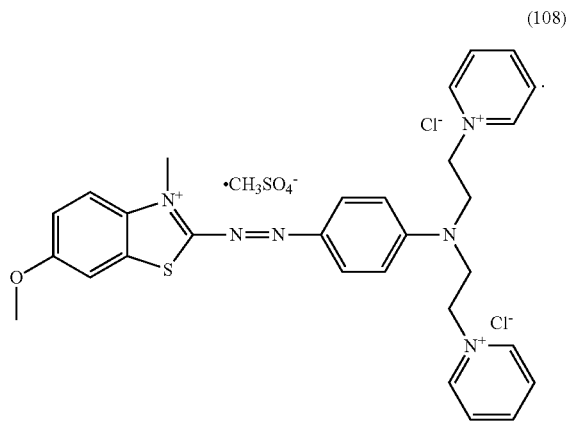

(108)

$^1$H NMR (CD$_3$OD, 400 MHz) δ=3.67 (s, 3H), 3.96 (s, 3H), 4.44 (m, 7H), 4.99 (t, 4H), 7.17 (d, J=9.2 Hz, 2H), 7.43 (dd, 1H), 7.73 (d, J=1.6 Hz, 1H), 8.07 (m, 3H), 8.12 (m, 4H), 8.6 (t, 2H), 9.1 (d, J=5.6 Hz, 4H). UV/VIS (water): $λ_{max}$ 582 nm.

Example A6

Step 1: Cs$_2$CO$_3$ (129.9 g) are added under stirring to a suspension of 3,4-dihydroxybenzaldehyde (10 g) and 3-dimethylaminopropylchloride hydrochloride (29.77 g) in acetone (350 ml) and the reaction mass is heated to reflux for 24 h (The reaction was monitored by TLC). The reaction mixture is filtered through a pad of Celite and the Celite pad is thoroughly washed with acetone (100 ml). The solvent is evaporated under reduced pressure and the resulting residue is subjected to column chromatography on silica gel (60-120 mesh) and eluted with chloroform:methanol (95:5 with few drops of NH$_4$OH) to give 12 g of a thick yellow oil of the formula

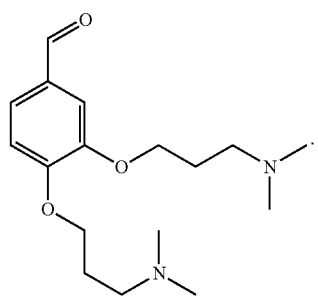

(109)

$^1$H NMR (DMSO-d$_6$, 400 MHz) δ 9.81 (s, 1H), 7.52 (d, J=8.4 Hz, 1H), 7.38 (s, 1H), 7.15 (d, J=8.4 Hz, 1H), 4.10 (t, 2H), 4.05 (t, 2H), 2.39 (t, 4H), 2.22 (d, 12H), 1.89 (m, 4H).

Step 2: γ-Picoline (8.52 g) is added drop wise to dimethyl sulfate (15 g) at room temperature and the reaction mixture is heated at 70° C. for 2 h and then cooled to room temperature (solid formation). Cold diethyl ether (25 ml) is added to the reaction mass and stirred for 0.5 h. Ether is decanted and the above step is repeated with cold diethyl ether (2×25 ml). The excess of solvent is removed under reduced pressure to get 19 g of a white hygroscopic solid.

$^1$H NMR (CD$_3$OD, 400 MHz) δ 8.67 (d, J=6 Hz, 2H), 7.86 (d, J=5.6 Hz, 2H), 4.25 (s, 3H), 3.60 (s, 3H), 2.62 (s, 3H).

Step 3: A solution of the compound prepared in the previous step (1.3 g), compound (109) (1.6 g) and piperidine (0.02 g) in methanol (20 ml) is refluxed for 15 h. After solvent evaporation the residue is stirred with ether (20 ml) for 0.5 h and the organic layer decanted. The above step is repeated twice. The product is dried under vacuum to obtain 1.1 g of a yellow solid of formula

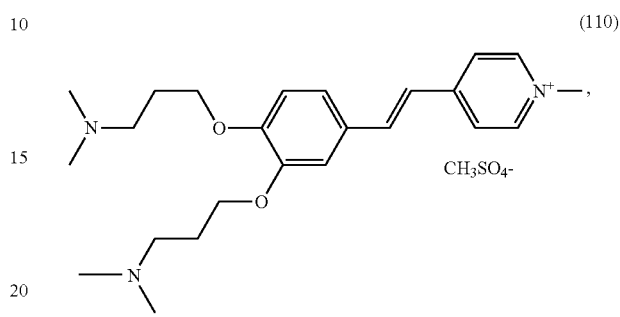

(110)

which can be used as such for dyeing hair.

$^1$H NMR (DMSO-d$_6$, 400 MHz) δ 8.78 (d, J=6 Hz, 2H), 8.11 (d, J=6 Hz, 2H), 7.89 (d, J=16 Hz, 1H), 7.36 (dd, J=16 Hz and 4.4 Hz, 2H), 7.29 (d, J=8.4 Hz, 1H), 7.05 (d, J=7.6 Hz, 1H), 4.21 (s, 3H), 4.05 (t, 4H), 2.49 (s, 3H), 2.38 (q, 4H), 2.14 (d, 12H), 1.78 (q, 4H).

Step 4: The compound of formula (110) (0.18 g) is stirred at room temperature with dimethyl sulfate (0.99 g) for 2 h. The reaction mixture is vigorously stirred with diethyl ether (4×25 ml) and the ether layer is decanted. Drying under vacuum affords 0.18 g of a yellow fluorescent dye of formula

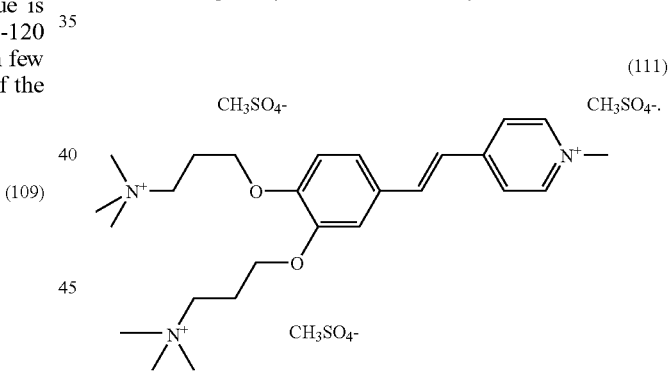

(111)

$^1$H NMR (CD$_3$OD, 400 MHz) δ 8.65 (d, J=6.8 Hz, 2H), 8.11 (d, J=7.2 Hz, 2H), 7.86 (d, J=16 Hz, 1H), 7.47 (s, 1H), 7.35 (m, 2H), 7.10 (d, J=8 Hz, 1H), 4.25 (m, 7H), 3.60 (m, 13H), 3.20 (d, 18H), 2.35 (m, 4H).

Example A7

Step 1: 3 g of the azo compound of the formula

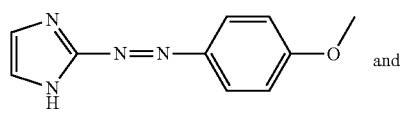

and 3.5 ml of epichlorohydrin are dissolved in 10 ml acetic acid. The mixture is stirred for 3 d at 50° C. After that time the acetic acid is evaporated under vacuum and the resulting oil is purified by column chromatography (alumina, ethyl acetate/methanol 10:2). After washing with acetone 0.94 g of a yellow powder of formula (112) are obtained. Analytical data: MS (EI+): m/z 387 (M+). UV/VIS(MeOH): λ$_{max}$ 408 nm.

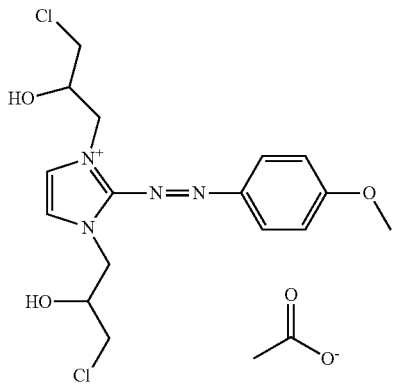
(112)

Step 2: 100 mg of the product from step 1 are refluxed in a mixture of 2 ml methanol and 0.73 ml diethylamine for 2 days.

After evaporation of the solvent 110 mg of a red powder of formula (113) are obtained. This compound can be used as such for the dyeing of hair.

Analytical data: MS (EI+): m/z 502 (M+). UV/VIS (MeOH): λ$_{max}$ 559 nm.

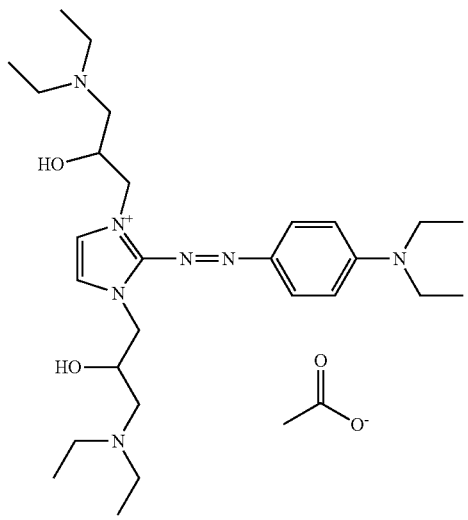
(113)

Step 3: 100 mg of the product obtained in step 1 are stirred with 50 μl methyl iodide in 10 ml chloroform for 12 h at room temperature.

The precipitate is collected by filtration and dried to obtain 130 mg of a red dye of formula (114).

MS (EI+): m/z 530 [M−2H]+. UV/VIS(MeOH): λ$_{max}$=560 nm.

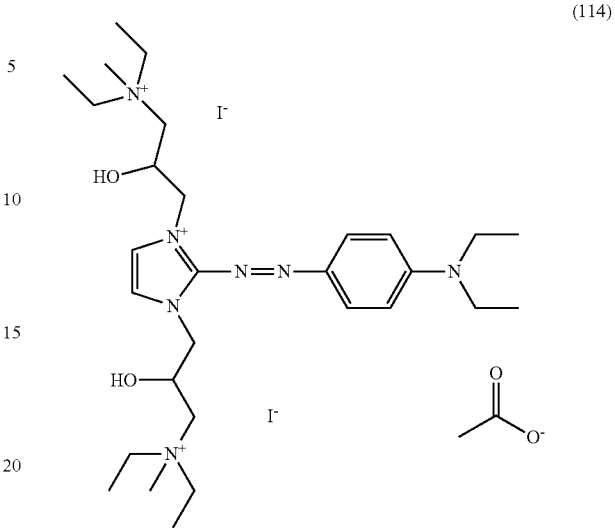
(114)

Example A8

Step 1: A solution of 5 g of the amine of the formula

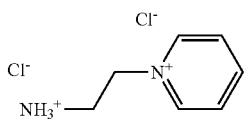

and 9.84 ml of triethylamine in 120 ml ethanol is cooled to 0° C.

Then 4.26 ml bromoacetyl chloride are added dropwise at 0° C.

After that the mixture is warmed slowly to room temperature and filtered.

The filtrate is evaporated to dryness to obtain 15.34 g of a colorless powder of formula (115).

Analytical data: 1H NMR (MeOH-d$_3$): δ[ppm] 9.04 (d, 2H), 8.66 (t, 1H), 8.16 (t, 2H), 4.82 (t, 2H), 4.04 (s, 2H), 3.87 (t, 2H)

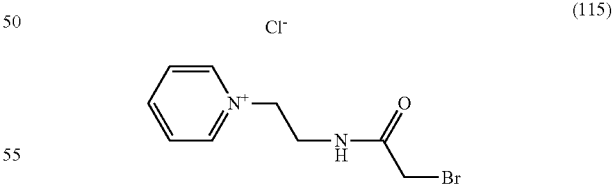
(115)

Step 2: A suspension of 100 mg of the azo compound of the formula

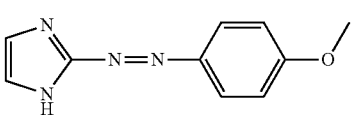

and 745 mg of the product obtained in step 1 in 2 ml chloroform are stirred for 2 days at 60° C.

The solvent is evaporated under vacuum and the residue is extracted with a small amount of ethanol.

The extract is evaporated to dryness to obtain 43 mg of a yellow powder of formula (116). MS (EI+): m/z 529 (M+). UV/VIS (MeOH): $\lambda_{max}$=393 nm.

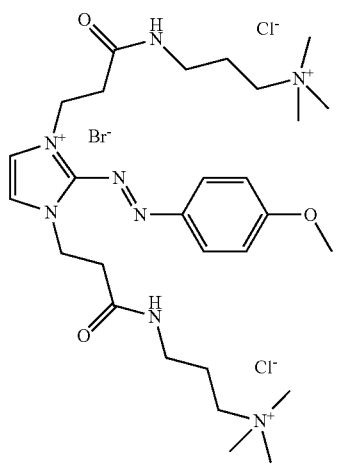

(116)

Step 3: The compound obtained in step 2 is stirred with 0.5 ml diethylamine in 4 ml ethanol at 70° C. for 4 h.

Than the reaction mixture is evaporated to dryness to obtain 350 mg of a red powder of formula (117).

MS (EI+): m/z 570 (M+). UV/VIS (MeOH): $\lambda_{max}$ 546 nm.

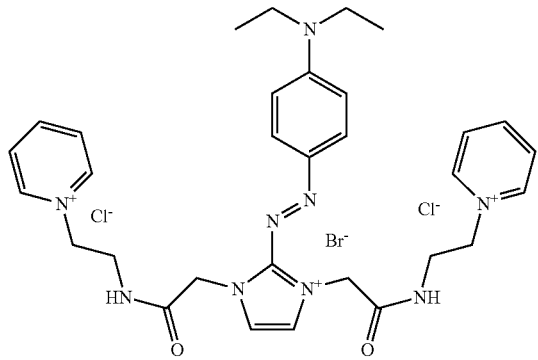

(117)

Example A9

Step 1: 2 g of the azo compound of the formula

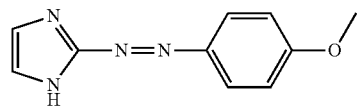

are dissolved in 50 ml acetone at 50° C.

To this solution 1.22 ml of hydrobromic acid (48%) are added dropwise at 50° C.

Then the reaction mixture is cooled to room temperature, the precipitate is collected by filtration and dried under vacuum to obtain 2.56 g of a brown powder.

Step 2: A suspension of 140 mg of the product from step 1, 5 mg of the azo compound of the formula

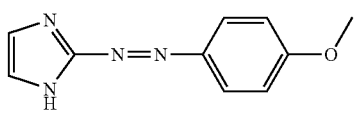

and 859 mg of (3-acrylamidopropyl)trimethylammonium chloride in 4 ml acetic acid are stirred at 80° C. for 2 days.

Then 10 ml hexane are added. The resulting oil is separated, washed with acetone and dried to obtain 962 mg of a yellow oil of the formula (118).

MS (EI+): m/z 543 [M−2H]+. UV/VIS (MeOH): $\lambda_{max}$=393 nm.

(118)

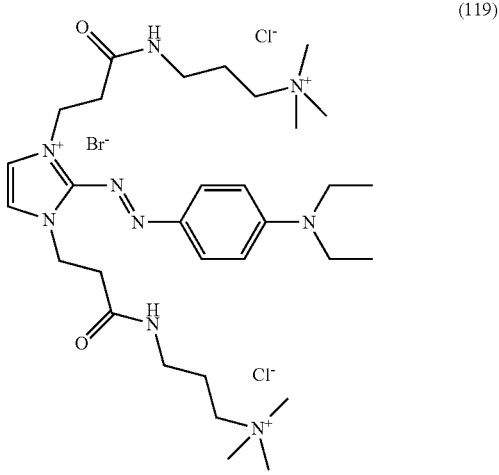

Step 3: The crude product obtained in step 2 is dissolved in 4 ml ethanol and stirred with 1.0 ml diethylamine under reflux for 10 h.

The reaction mixture is evaporated to dryness and the residue is purified by column chromatography (alumina, EE/MeOH 4:1).

A red zone is collected and evaporated to dryness to obtain 30 mg of a red compound of formula (119).

MS (EI+): m/z 584 [M−2H]+. UV/VIS (MeOH): $\lambda_{max}$=544 nm.

(119)

Example A10

Step 1: A solution of 483 mg of the azo compound of formula

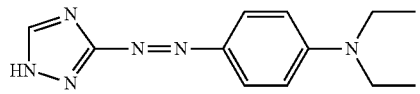

and 340 ml of epichlorohydrin in 2 ml acetic acid are stirred for 2 days at 80° C. The solvent is evaporated under vacuum and the remaining oil is dissolved in acetone.

Ether is added to the solution until the product separates as an oil.

The oil is dried under vacuum to obtain 850 mg of a red powder of formula (120).

MS (EI+): m/z 429, 431, 433 (M+). UV/VIS (MeOH): $\lambda_{max}$=543 nm.

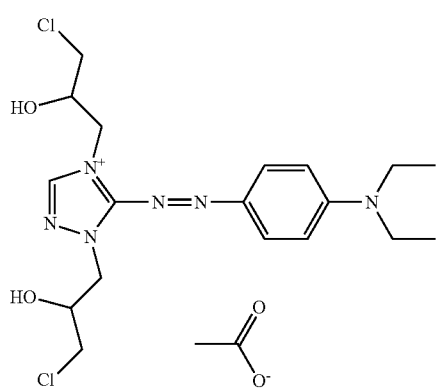

(120)

Step 2: The compound obtained in step 1 is stirred for 2 days at 100° C. in 3 ml pyridine.

Then the solvent is evaporated and the residue is dissolved in methanol and evaporated to dryness again.

The crude product is washed with acetone and dried to obtain 319 mg of a red powder of formula (121).

MS (EI+): m/z 515 [M−2H]+. UV/VIS (MeOH): $\lambda_{max}$=515 nm.

(121)

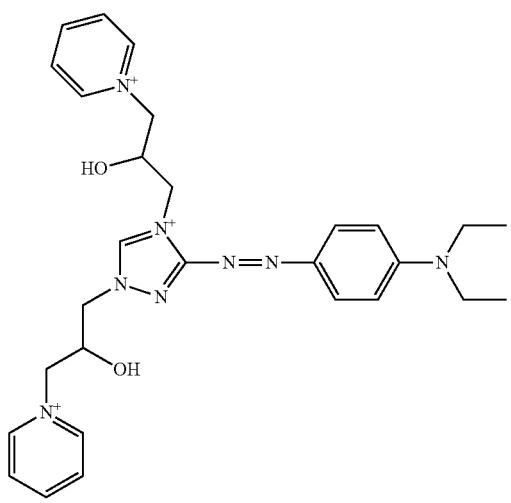

Example A11

Step 1: 2.9 ml of hydrobromic acid (48%) are added dropwise to a solution of 5 g of the pyridine derivative of formula

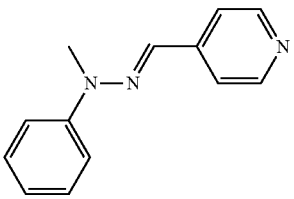

in 80 ml acetone.

After 1 h stirring at room temperature the yellow precipitate is filtered off and dried under vacuum to obtain 6.67 g of a yellow powder.

Step 2: A solution of 1 g of the product from step 1, 34 mg of the free pyridine base of the formula

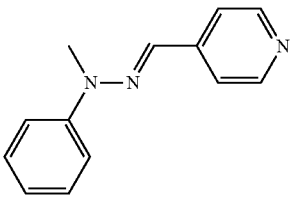

and 4.75 g of the acrylamide derivative of the formula

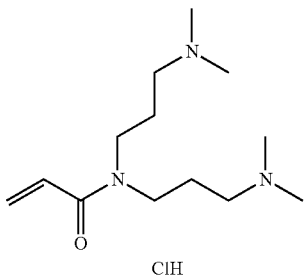

in 20 ml acetic acid are stirred for 20 h at 80° C. The acetic acid is evaporated under vacuum and the remaining oil is treated with a 25 ml acetone and dried. This compound can be used as such for the dyeing of hair.

Analytical data: MS (EI+): m/z 453 (M+). UV/VIS (MeOH): $\lambda_{max}$=425 nm.

(122)

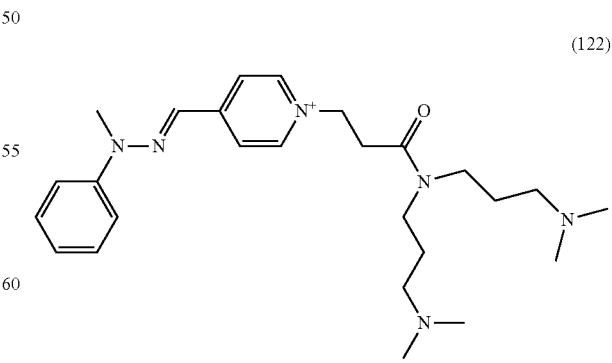

Step 3: 1 g of the product obtained in step 2 is dissolved in 50 ml chloroform and stirred with 1.25 ml methyl iodide for 12 h at room temperature.

Then the precipitate is collected by filtration and dried under vacuum to obtain 0.9 g of a yellow powder of formula (123).

Analytical data: MS (EI+): m/z 481 [M−2H]+. UV/VIS (MeOH): $\lambda_{max}$=421 nm.

(123)

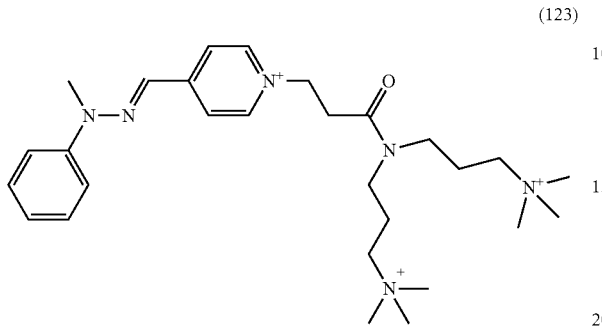

Example A12

Step 1: A solution of 7.69 g pyridine derivative of the formula

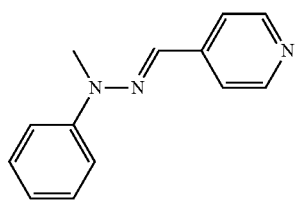

and 37 ml 1,3-dibromopropane in 150 ml methylethyl ketone are stirred for 5 h at 85° C.

Then the reaction mixture is diluted with 50 ml methylethyl ketone.

The precipitate is filtered off and washed with methylethyl ketone.

The crude product is stirred for 2 h in 70 ml ethanol at room temperature.

The suspension is filtered off and the filtrate is evaporated to dryness to obtain 7.41 g of a yellow compound of formula (124).

MS (EI+): m/z 332, 334 [M]+. UV/VIS (MeOH): $\lambda_{max}$=423 nm.

(124)

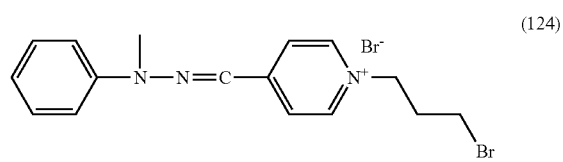

Step 2: A solution of 100 mg of the product obtained in step 1 and 0.1 ml 3,3′-imino-bis-(N,N-dimethylpropylamine) in 2 ml chloroform are stirred for 13 h at room temperature and than for 30 min at 60° C.

Then the solvent is evaporated under vacuum and the residue is washed with ethyl acetate to obtain 90 mg of a yellow compound of formula (125).

MS (EI+): m/z 440 [M+1]+. UV/VIS (MeOH): $\lambda_{max}$=423 nm.

(125)

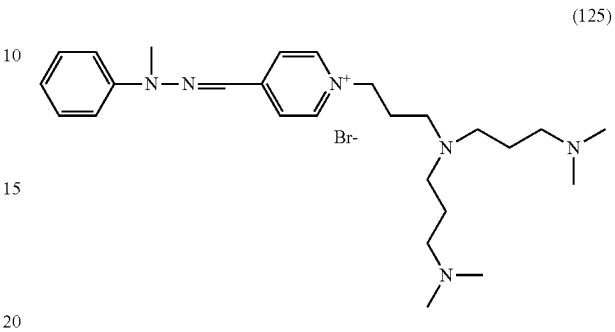

Step 3: 90 mg of the product obtained in step 1 are stirred with 50 µl methyl iodide in 2 ml chloroform for 12 h at room temperature.

The precipitate is collected by filtration and dried to obtain 128 mg of a yellow substance of formula (126).

MS (EI+): m/z 467 [M−2H]+. UV/VIS (MeOH): $\lambda_{max}$=423 nm.

(126)

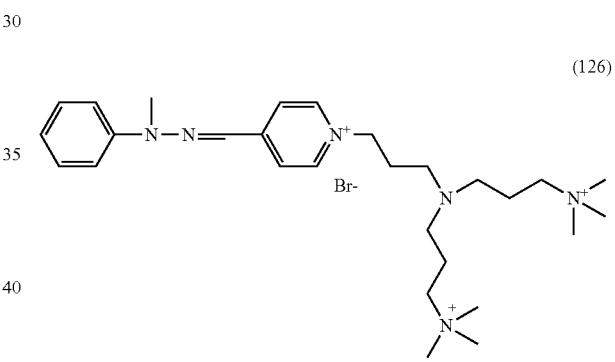

Example A13

Reaction scheme:

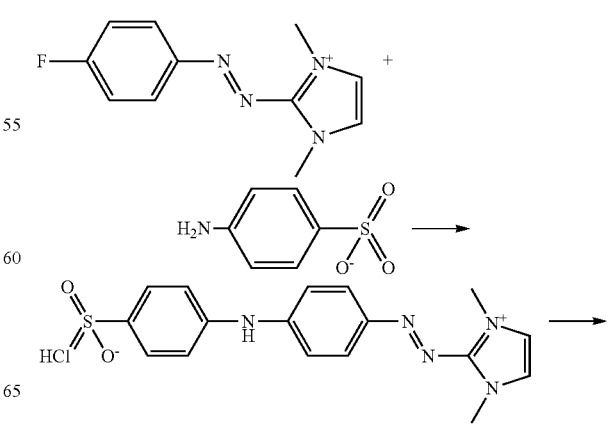

-continued

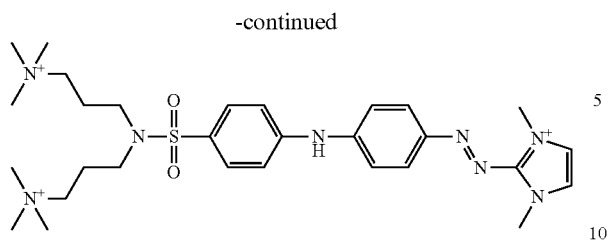

124 g of educt (1)(=fluoro derivative) are introduced in 400 g dimethylacete amide and 86.6 g sulfonic acid derivative. The reaction mass is warmed up to 80° C. and 88 g DABCO (1,4-diazabicyclo[2,2,2]octane) are added through dropping funnel.

Keeping at this temperature the reaction is completed after 3 h, the reaction mass is cooled to room temperature and separated through filtration, washed with acetonitrile and dried in vacuum to obtain 247 g of the solid material.

This material is suspended in 1000 ml dimethylformamide, cooled to 0° C. and then 225 g thionyl chloride are introduced maintaining the temperature with external cooling.

The reaction mass is stirred and warmed up to room temperature and held for 2 more hours. Gases are stripped off by vacuum and 130 g bis(dimethylaminopropyl)amine are dropped in, the temperature rises to 35° C.

After 2 h at room temperature the reaction mass is quaternized with dimethylsulfate and then separated by filtration, washed with acetonitrile and dried to obtain 350 g of a dark red material with the desired structure.

Example A14

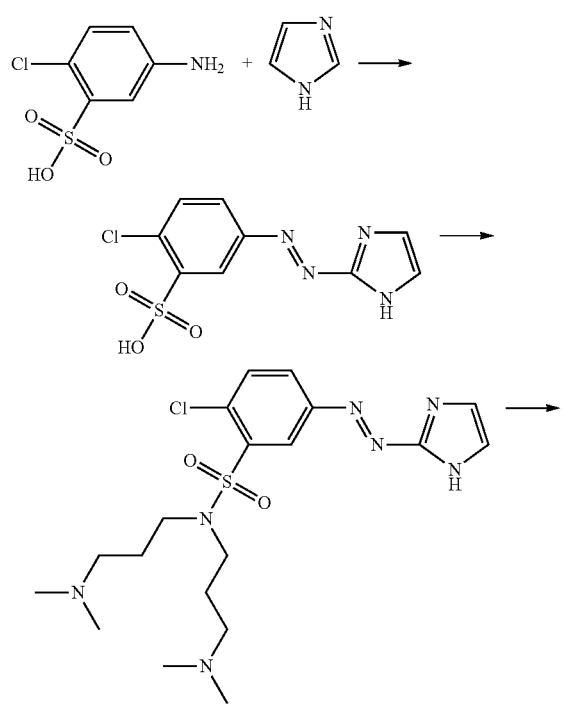

-continued

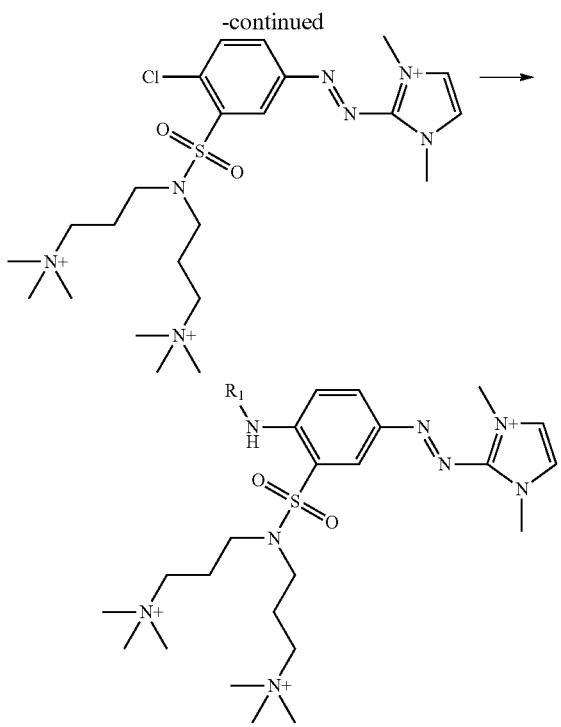

212 g 4-chloroaniline sulfonic acid are added to 500 ml water, warmed up to 50° C. and 57 g sodium carbonate are added.

Then the good stirred mixture is cooled to 0° C. and 257 g hydrochloric acid are added fast, the temperature rises to 10° C.

During 40 minutes 150 ml sodium nitride (37%) are added at 0-5° C. and the reaction is finished within 1 h.

The solution is poured within 75 min into a cooled and good mixed solution of 71 g imidazole in 100 ml water.

The pH is hold at 9.0 with 95 ml of a solution of 36% sodium hydroxide.

After 2 h the product is isolated with 300 g sodium chloride at 0° C.

The suspension is filtered off, washed with salt solution and dried to obtain 265 g of the product.

This material is suspended in 1000 ml dimethylformamide, cooled to 0° C. and then 225 g thionyl chloride are introduced, maintaining the temperature through external cooling.

The reaction mass is stirred and warmed up to room temperature, hold for 2 more h, then gases are stripped off through vacuum and 130 g bis(dimethylaminopropyl)amine are dropped in, the temperature rises to 35° C.

After 2 h at room temperature the reaction mass is quaternized with dimethylsulfate and then separated by filtration, washed with acetonitrile and dried to obtain 350 g of a dark red material with the desired structure.

The last step is the substitution with a primary or secondary amine of the aromatic chlorine which is realized in dimethylformamide as solvent, with an excess of amine at 50-80° C. After the long reaction time of 10 to 24 h the product is separated by filtration, washed with acetonitrile and dried.

B. Application Examples

For the application examples the following hair types have been used:
1 blonde hair tress (VIRGIN White Hair),
1 middle blonde hair tress (UNA-Europ. nature hair, Color middle blonde),
1 bleached hair tress (UNA-Europ. nature hair, Color white bleached).

The wash- and light fastness of the dyed hair is evaluated by the Grey scale according to: Industrial Organic Pigments by Herbst&Hunger, 2nd ed., p. 61, Nr 10: DIN 54 001-8-1982, "Herstellung und Bewertung der Änderung der Farbe", ISO 105-A02-1993.

Coloring Solution pH 9.5:
0.1% w/w of one of the dyes described in examples A1 to A6 are dissolved in a Plantaren solution (10% w/w Plantacare 200UP (ID: 185971.5) in water; pH adjusted to 9.5 with 50% citric acid solution or monoethanolamine solution).

Coloring Solution pH 5.5:
0.1% w/w of one of the dyes described in examples A1 to A6 are dissolved in a Plantaren solution (10% w/w Plantacare 200UP (ID: 185971.5) in water; pH adjusted to 5.5 with 50% citric acid solution or monoethanolamine solution).

Coloring Solution pH 3.0:
0.1% w/w of one of the dyes described in examples A1 to A6 are dissolved in a Plantaren solution (10% w/w Plantacare 200UP (ID: 185971.5) in water; pH adjusted to 3.0 with 50% citric acid solution or monoethanolamine solution).

Coloring Cream:

|  | % w/w |
| --- | --- |
| Cetearyl Alcohol | 11.0 |
| Oleth-5 | 5.0 |
| Oleic acid | 2.5 |
| Stearamide MEA | 2.5 |
| Cocamide MEA | 2.5 |
| Propylene Glycol | 1.0 |
| Ammonium chloride | 0.5 |
| Tetrasodium EDTA | 0.2 |
| Silica | 0.1 |
| Water | ad 100 |
| Dyestuff | 1.0 |

Directly before the dyeing the color cream is mixed with hydrogen peroxide 6% in a ratio 1:1. Then this mixture is applied to the hair tresses.

The hair tresses are dyed according to the following procedure:

The coloring solution with pH 9.5, 5.5 or 3.0 of the color cream (1:1 mixture with 6% hydrogen peroxide solution) is applied directly to the dry hair, incubated for 20 min at room temperature, and then rinsed off under tap water (Water temperature: 37° C.+/−1° C.; flow rate of water: 5-6 l/min.). Then it is pressed out with a paper towel and dried over night at room temperature on a glass plate.

To determine the wash fastness two sets of hair tresses are dyed under the same conditions. One set of the dyed tresses is washed with a commercial shampoo (GOLDWELL definition Color & Highlights, color-conditioner shampoo) using approx. 0.5 g shampoo for each tress under tap water (water temperature: 37° C.+/−1° C.; flow rate 5-6 l/min).

Finally the tresses are rinsed under tap water, pressed out with a paper towel, combed and dried with a hair dryer or at room temperature.

This procedure is repeated 10 times. Then the color loss of the set of washed tresses relative to the set of unwashed tresses is evaluated using the Grey Scale.

For determination of the light fastness a hair tress colored by one of the procedures described above is fixed on a carton and covered partly with a carton. Then the tress is exposed to light using an ATLAS Suntest XLS+ for 8 hours.

The color loss of the uncovered part relative to the covered part of the tress is evaluated using the Grey Scale.

The specific conditions of the application examples and the results are given in Table 1.

TABLE 1

Application Examples

| Example No. | Formula No. | Coloring Solution/ Cream | Hair Type | Color | Intensity | Brilliance | Wash-fastness | Light-fastness |
| --- | --- | --- | --- | --- | --- | --- | --- | --- |
| B1 | (102) | pH 3.0 | blond | red | bad | bad | 1 | 5 |
|  |  |  | middle blond | red | good | good | 1-2 | 5 |
|  |  |  | bleached | red | good | good | 2-3 | 5 |
| B2 | (102) | pH 5.5 | blond | red | good | good | 2-3 | 5 |
|  |  |  | middle blond | red | good | good | 2-3 | 5 |
|  |  |  | bleached | red | good | good | 2-3 | 5 |
| B3 | (102) | pH 9.5 | blond | red | good | good | 3-4 | 5 |
|  |  |  | middle blond | red | good | good | 4 | 5 |
|  |  |  | bleached | red | good | good | 3 | 5 |
| B4 | (103) | pH 9.5 | blond | red | good | good | 4 | — |
|  |  |  | middle blond | red | good | good | 4 | — |
|  |  |  | bleached | red | good | good | 2-3 | — |
| B5 | (104) | pH 9.5 | blond | red | good | good | 4 | — |
|  |  |  | middle blond | red | good | good | 4 | — |
|  |  |  | bleached | red | good | good | 3 |  |

TABLE 1-continued

Application Examples

| Example No. | Formula No. | Coloring Solution/ Cream | Hair Type | Color | Intensity | Brilliance | Wash-fastness | Light-fastness |
|---|---|---|---|---|---|---|---|---|
| B6 | (105) | pH 9.5 | blond | green | good | good | 3 | |
| | | | middle blond | green | good | good | 2-3 | |
| | | | bleached | green | good | good | 2-3 | |
| B7 | (108) | pH 9.5 | blond | green | good | good | 3 | 3-4 |
| | | | middle blond | green | good | good | 2-3 | 4 |
| | | | bleached | green | good | good | 3 (green) | 4-5 |
| B8 | (110) | pH 9.5 | blond | yellow | moderate | good | 3 | — |
| | | | middle blond | yellow | moderate | good | 4 | — |
| | | | bleached | yellow | moderate | good | 2 | — |
| B9 | (102) | Color cream | blond | red | good | good | 4-5 | — |
| | | | middle blond | red | good | good | 4 | — |
| | | | bleached | red | good | good | 2-3 | — |
| B10 | (121) | pH 9.5 | blond | red | good | good | 4 | — |
| | | | middle blond | red | good | good | 3 | — |
| | | | bleached | red | good | good | 2-3 | — |
| B11 | (119) | pH 9.5 | blond | red | good | good | 3-4 | — |
| | | | middle blond | red | good | good | 1-2 | — |
| | | | bleached | red | good | good | 1-2 | — |

The invention claimed is:

1. Compounds of formula $$[D-E_1{=}E_2-K]^{3+} \quad An_1^-\ An_2^-;\ An_3^- \quad \text{wherein} \tag{1}$$

D is an aromatic or a cationic heteroaromatic group, which is optionally substituted by one or more than one $C_1$-$C_{14}$alkyl, $C_1$-$C_{14}$alkoxy, hydroxy-$C_1$-$C_{14}$alkyl, $C_3$-$C_8$cycloalkyl, —CN, $NO_2$, —$NR_3R_4$, halogen, $C_6$-$C_{10}$aryl, which is optionally substituted or $C_1$-$C_{14}$alkyl, or by one or more groups Z;

$E_1$ and $E_2$ independently from each other are =CH; or =N—;

K is an aromatic or heteroaromatic group which is optionally substituted by one or more than one $C_1$-$C_{14}$alkyl, $C_1$-$C_{14}$alkoxy, $C_3$-$C_8$cycloalkyl, $C_6$-$C_{10}$aryl, halogen, hydroxy, $NO_2$, —$NR_3R_4$, —$N(R_3)(CO)R_4$, —$SO_2NR_3R_4$, —$SONR_3R_4$ or by one or more Z; or a radical of formula —$NR_1R_2$;

$R_1$ and $R_2$ independently from each other are hydrogen; $C_1$-$C_{14}$alkyl; cyclo-$C_1$-$C_{14}$alkyl; $C_6$-$C_{10}$aryl; an aromatic or heteroaromatic group which is optionally substituted by one or more than one $C_1$-$C_{14}$alkyl, $C_1$-$C_{14}$alkoxy, $C_3$-$C_8$cycloalkyl, $C_6$-$C_{10}$aryl, halogen, hydroxy, —$NR_5R_6$, —$N(R_5)$—$(CO)R_5$ or by Z;

Z is a group of the formula (1a) *—$X_1$—$Y_1$—$W_1$, wherein $X_1$ is the direct bond; —$NR_7$—; —O—; —$NR_7(C{=}O)$—; —(CO)$NR_7$—; —O(C=O)—; —(CO)O—; or —(C=O)—;

$Y_1$ is the direct bond; $C_1$-$C_{12}$alkylene, which is optionally interrupted by —O—, —$NR_8$—, —S—, —(C=O)—, —O(C=O)—, (C=O)O—, —$NR_7(C{=}O)$—, —(C=O)$NR_7$—, and which may substituted by $C_1$-$C_{14}$alkyl, hydroxy-$C_1$-$C_{14}$alkyl, hydroxy, —$NR_9R_{10}$ or halogen; or $C_6$-$C_{10}$arylene, which may substituted by $C_1$-$C_{14}$alkyl, hydroxy-$C_1$-$C_{14}$alkyl, hydroxy, amino or halogen;

$W_1$ is a cationic group; and $R_3, R_4, R_5, R_6, R_7, R_8, R_9$ and $R_{10}$ independently from each other are hydrogen; $C_1$-$C_{14}$alkyl; or Z; and $An_1^-, An_2^-$ and $An_3^-$ independently from each other are an anion with the proviso that 2 radicals represent Z in order to obtain an overall charge of $3^+$.

2. Compounds according to claim 1, wherein said compounds are selected from the group consisting of formula $$[D{-}N{=}N{-}K]^{3+} \quad An_1^-\ An_2^-;\ An_3^- \tag{2}$$

$$[D{-}C{=}C{-}K]^{3+} \quad An_1^-\ An_2^-;\ \text{and}\ An_3^- \tag{3}$$

$$\left[D{-}C{=}N{-}\underset{R_1}{N}{-}R_2\right]^{3+} \quad An_1^-\ An_2^-;\ \text{wherein}\ An_3^- \tag{4}$$

D, K, $R_1, R_2, An_1^-, An_2^-$ and $An_3^-$ are defined in claim 1.

3. Compounds according to claim 1 wherein
D is selected from the group consisting of formula
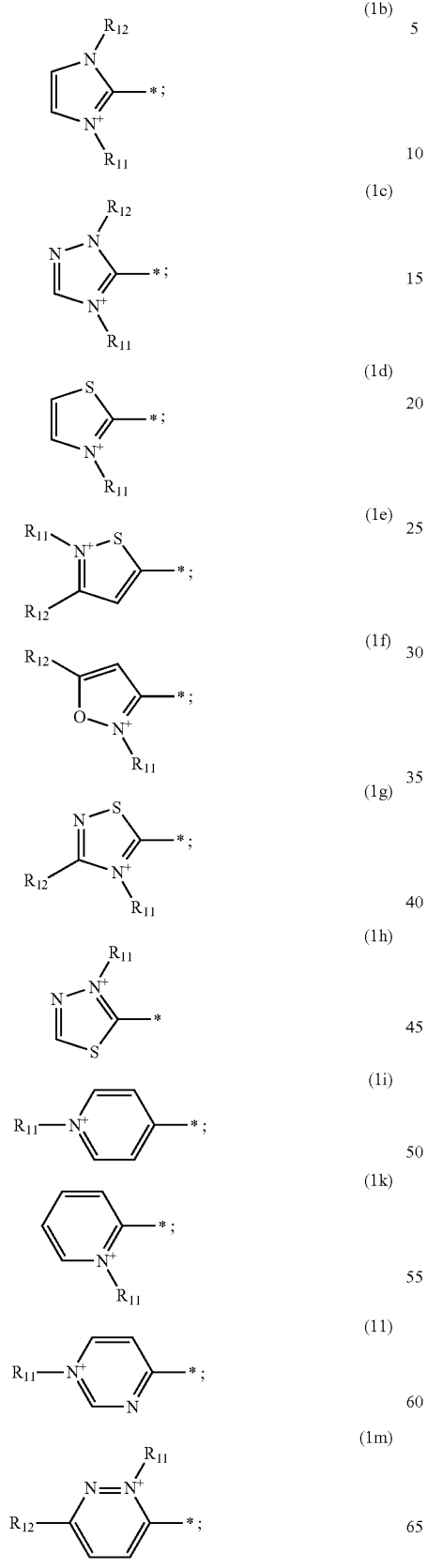
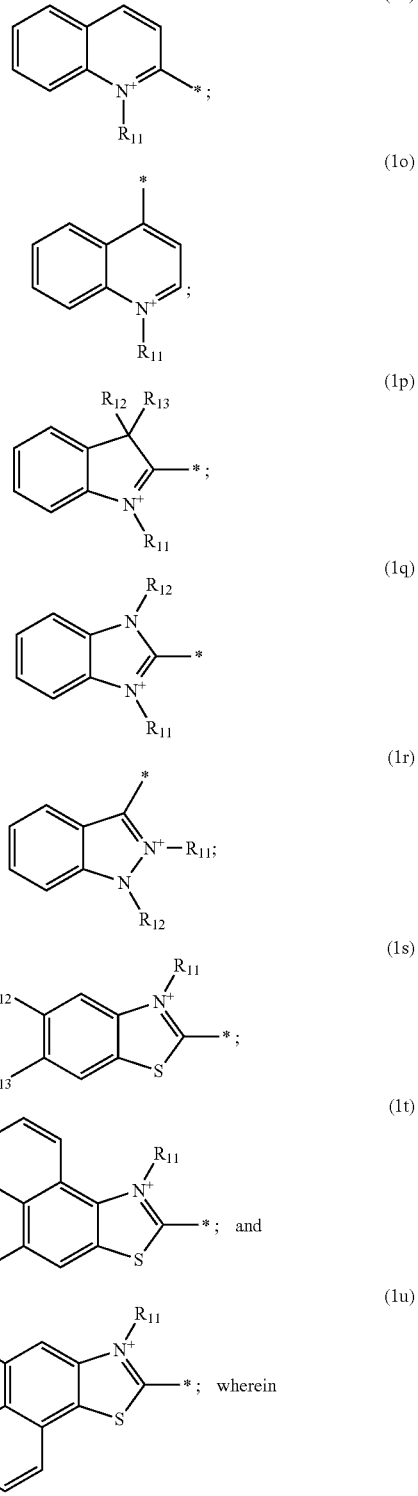
$R_{11}$ is unsubstituted or OH—, $C_1$-$C_{14}$alkoxy-, halogen- CN— or $NR_{14}R_{15}$— substituted $C_1$-$C_{14}$alkyl; or Z;
$R_{12}$ and $R_{13}$ independently from each other are hydrogen; or unsubstituted or OH—, $C_1$-$C_{14}$alkoxy-, halogen-, CN—, $NR_{16}R_{17}$— substituted $C_1$-$C_{14}$alkyl; $C_1$-$C_{14}$alkoxy; or Z;

$R_{14}$, $R_{15}$, $R_{16}$ and $R_{17}$ independently from each other are hydrogen; or $C_1$-$C_{14}$alkyl; and Z is defined as in claim 1.

4. Compounds according to claim 1, wherein

K is phenyl or naphtyl, which may be substituted by $C_1$-$C_{14}$alkyl, $C_1$-$C_{14}$alkoxy, $C_3$-$C_8$cycloalkyl, $C_6$-$C_{10}$aryl, halogen, hydroxy, —$NR_3R_4$, —$N(R_3)$—$(CO)R_4$; or by one or more groups Z; wherein $R_3$, $R_4$, and Z are defined as in claim 1.

5. Compounds according to claim 1 wherein

Z is ($C_1$-$C_5$alkylene)-$W_1$; wherein $C_1$-$C_5$alkylene may be interrupted by —O— or —$NR_8$— or substituted by OH; and $W_1$ and $R_8$ are defined as in claim 1.

6. Compounds according to claim 1 wherein $W_1$ is an aliphatic ammonium group or a cationic heteroaromatic group.

7. Compounds according to claim 6, wherein $W_1$ is selected from the group consisting of

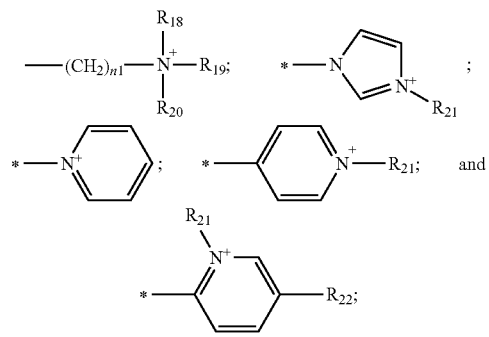

wherein $R_{18}$, $R_{19}$, $R_{20}$, $R_{21}$ and $R_{22}$ are hydrogen; or $C_1$-$C_{14}$alkyl; and n1 is a number from 0 to 4.

8. Compounds according to claim 1, wherein

Z is selected from the group consisting of

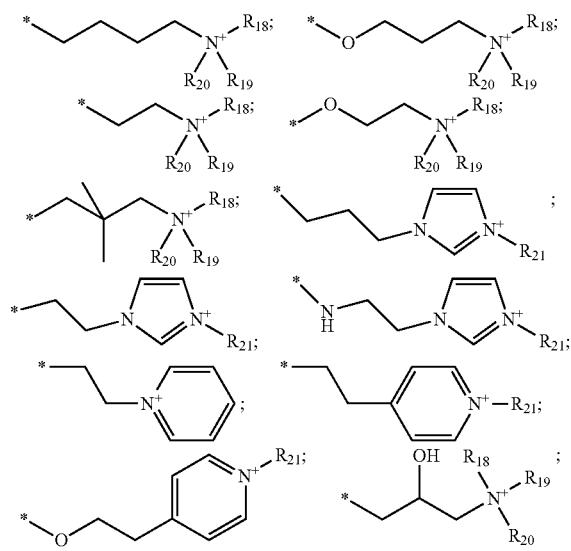

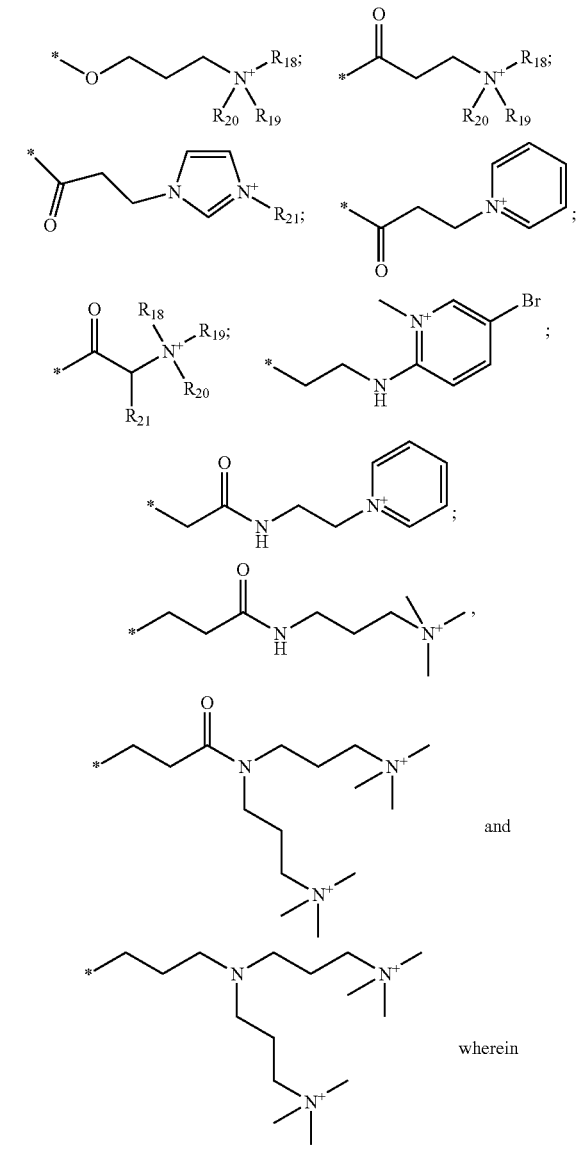

$R_{18}$, $R_{19}$, $R_{20}$, and $R_{21}$ are hydrogen; or $C_1$-$C_{14}$alkyl.

9. Compounds according to claim 1, wherein said compounds are selected from the group consisting of formula

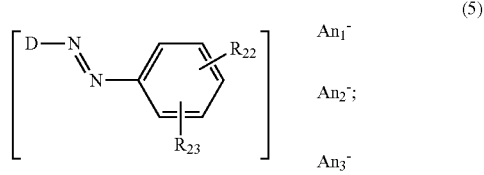

(5)

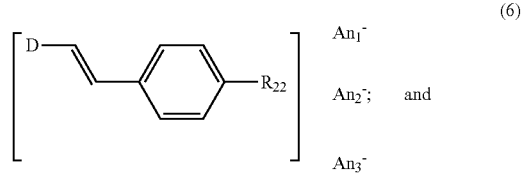

(6)

-continued

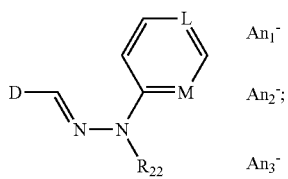
(7)

wherein $R_{22}$ and $R_{23}$ independently from each other are *—$X_1$—$Y_1$—$W_1$;

L and M, independently from each other are —C=; or —$N^+(R_{24})$=;

$R_{24}$ is hydrogen; or $C_1$-$C_{14}$alkyl; and

D, $X_1$, $Y_1$ and W are defined as in claim 1.

10. Compounds according to claim 1, wherein said compounds are selected from the group consisting of formula (8)

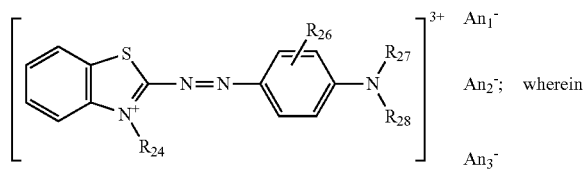

(9)

(10)

$R_{24}$, $R_{25}$, $R_{26}$, $R_{27}$ and $R_{28}$ independently from each other are hydrogen; $C_1$-$C_5$alkyl; hydroxy-$C_1$-$C_5$alkyl; hydroxy; halogen; $C_4$-$C_6$cycloalkyl; $C_6$-$C_{10}$aryl optionally containing heteroatoms; or Z; and $An_1^-$, $An_2^-$ and $An_3^-$ and Z are defined as in claim 1;
with the proviso that 2 radicals represent Z in order to obtain an overall charge of $3^+$.

11. Compounds according to claim 1, wherein said compounds are selected from the group consisting of formula

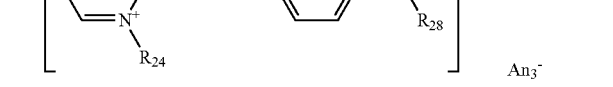
(11)

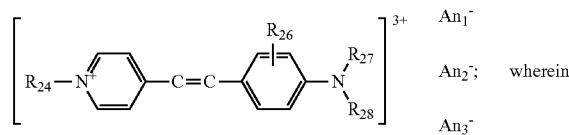
(12)

$R_{24}$, $R_{26}$, $R_{27}$ and $R_{28}$ independently from each other are hydrogen; $C_1$-$C_{14}$alkyl; hydroxy-$C_1$-$C_{14}$alkyl; hydroxy; halogen; $C_4$-$C_6$cycloalkyl; $C_6$-$C_{10}$aryl optionally containing heteroatoms; or Z; and Z and $An_1^-$, $An_2^-$ and $An_3^-$ are defined as in claim 1;
with the proviso that 2 radicals represent Z in order to obtain an overall charge of $3^+$.

12. Compounds according to claim 1, wherein said compounds are selected from the group consisting of formula

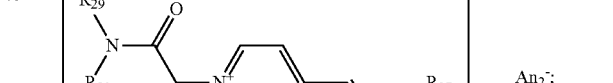
(13)

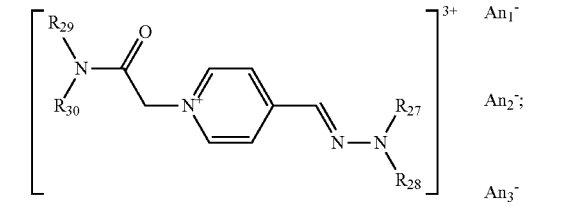
(14)

wherein

L and M independently from each other are —C=; or —$N^+(R_{24})$=;

$R_{27}$, $R_{28}$, $R_{29}$ and $R_{30}$ independently from each other are hydrogen; $C_1$-$C_{14}$alkyl; hydroxy-$C_1$-$C_{14}$alkyl; hydroxy; halogen; cyclo-$C_3$-$C_8$alkyl; or $C_6$-$C_{10}$aryl, which optionally contains hetero atoms; or a group Z;

$R_{24}$ is hydrogen; or $C_1$-$C_{14}$alkyl; and $An_1^-$, $An_2^-$ and $An_3^-$ and Z are defined as in claim 1;
with the proviso that 2 radicals represent Z in order to obtain an overall charge of $3^+$.

13. A composition comprising at least one dye of formula (1) according to claim 1.

14. A composition according to claim 13 further comprising at least one single further direct dye and/or an oxidative agent.

15. A composition according to claim 13 further comprising at least one single oxidative dye and/or at least one single oxidative dye and an oxidative agent.

16. A composition according to claim 13 in form of a shampoo, a conditioner, a gel or an emulsion.

17. A method of dyeing organic material, which comprises treating the organic material with at least one dye of formula (1)

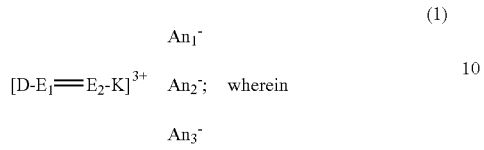

wherein

- D is an aromatic or a cationic heteroaromatic group, which is optionally substituted by one or more than one $C_1$-$C_{14}$alkyl, $C_1$-$C_{14}$alkoxy, hydroxy-$C_1$-$C_{14}$alkyl, $C_3$-$C_8$cycloalkyl, —CN, $NO_2$, —$NR_3R_4$, halogen, $C_6$-$C_{10}$aryl, which is optionally substituted or $C_1$-$C_{14}$alkyl, or by one or more groups Z;
- $E_1$ and $E_2$ independently from each other are =CH; or =N—;
- K is an aromatic or heteroaromatic group which is optionally substituted by one or more than one $C_1$-$C_{14}$alkyl, $C_1$-$C_{14}$alkoxy, $C_3$-$C_8$cycloalkyl, $C_6$-$C_{10}$aryl, halogen, hydroxy, $NO_2$, —$NR_3R_4$, —$N(R_3)(CO)R_4$, —$SO_2NR_3R_4$, —$SONR_3R_4$ or by one or more Z; or a radical of formula —$NR_1R_2$;
- $R_1$ and $R_2$ independently from each other are hydrogen; $C_1$-$C_{14}$alkyl; cyclo-$C_1$-$C_{14}$alkyl; $C_6$-$C_{10}$aryl; an aromatic or heteroaromatic group which is optionally substituted by one or more than one $C_1$-$C_{14}$alkyl, $C_1$-$C_{14}$alkoxy, $C_{1\text{-}3}$—$C_8$cycloalkyl, $C_6$-$C_{10}$aryl, halogen, hydroxy, —$NR_5R_6$, —$NR_5(R_5)$—$(CO)R_5$ or by Z;
- Z is a group of the formula (1a) *—$X_1$—$Y_1$—$W_1$, wherein $X_1$ is the direct bond; —$NR_7$—; —O—; —$NR_7(C=O)$—; —$(CO)NR_7$—; —$O(C=O)$—; —$(CO)O$—; or —$(C=O)$—;
- $Y_1$ is the direct bond; $C_1$-$C_{12}$alkylene, which is optionally interrupted by —O—, —$NR_8$, —S—, —$(C=O)$—, —$O(C=O)$—, $(C=O)O$—, —$NR_7(C=O)$—, —$(C=O)NR_7$—, and which may substituted by $C_1$-$C_{14}$alkyl, hydroxy-$C_1$-$C_{14}$alkyl, hydroxy, —$NR_9R_{10}$ or halogen; or $C_6$-$C_{10}$arylene, which may substituted by $C_1$-$C_{14}$alkyl, hydroxy-$C_1$-$C_{14}$alkyl, hydroxy, amino or halogen;
- $W_1$ is a cationic group; and
- $R_3, R_4, R_5, R_6, R_7, R_8, R_9$ and $R_{10}$ independently from each other are hydrogen; $C_1$-$C_{14}$alkyl; or Z; and
- $An_1^-$, $An_2^-$ and $An_3^-$ independently from each other are an anion with the proviso that 2 radicals represent Z in order to obtain an overall charge of $3^+$.

18. A method according to claim 17, which comprises treating the organic material with at least one dye of formula (1) and an oxidative agent and, optionally, a further direct dye.

19. A method according to claim 17, which comprises treating the organic material with at least one compound of formula (1) and at least one single oxidative dye, or treating the organic material with a dye of formula (1) and at least one single oxidative dye and an oxidative agent.

20. A method according to claim 17 wherein the organic material is selected from keratin-containing fibers.

21. A method according to claim 20 wherein the keratin-containing fiber is human hair.

22. A method of dyeing organic material, which comprises treating the organic material with a composition comprising at least one dye of formula (1)

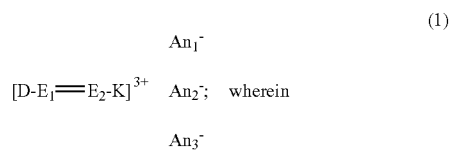

wherein

- D is an aromatic or a cationic heteroaromatic group, which is optionally substituted by one or more than one $C_1$-$C_{14}$alkyl, $C_1$-$C_{14}$alkoxy, hydroxy-$C_1$-$C_{14}$alkyl, $C_3$-$C_8$cycloalkyl, —CN, $NO_2$, —$NR_3R_4$, halogen, $C_6$-$C_{10}$aryl, which is optionally substituted or $C_1$-$C_{14}$alkyl, or by one or more groups Z;
- $E_1$ and $E_2$ independently from each other are =CH; or =N—;
- K is an aromatic or heteroaromatic group which is optionally substituted by one or more than one $C_1$-$C_{14}$alkyl, $C_1$-$C_{14}$alkoxy, $C_3$-$C_8$cycloalkyl, $C_6$-$C_{10}$aryl, halogen, hydroxy, $NO_2$, —$NR_3R_4$, —$N(R_3)(CO)R_4$, —$SO_2NR_3R_4$, —$SONR_3R_4$ or by one or more Z; or a radical of formula —$NR_1R_2$;
- $R_1$ and $R_2$ independently from each other are hydrogen; $C_1$-$C_{14}$alkyl; cyclo-$C_1$-$C_{14}$alkyl; $C_6$-$C_{10}$aryl; an aromatic or heteroaromatic group which is optionally substituted by one or more than one $C_1$-$C_{14}$alkyl, $C_1$-$C_{14}$alkoxy, $C_3$-$C_8$cycloalkyl, $C_6$-$C_{10}$aryl, halogen, hydroxy, —$NR_5R_6$, —$N(R_5)$—$(CO)R_5$ or by Z;
- Z is a group of the formula (1a) *—$X_1$—$Y_1$—$W_1$, wherein $X_1$ is the direct bond; —$NR_7$—; —O—; —$NR_7(C=O)$—; —$(CO)NR_7$—; —$O(C=O)$—; —$(CO)O$—; or —$(C=O)$—;
- $Y_1$ is the direct bond; $C_1$-$C_{12}$alkylene, which is optionally interrupted by —O—, —$NR_8$, —S—, —$(C=O)$—, —$O(C=O)$—, $(C=O)O$—, —$NR_7(C=O)$—, —$(C=O)NR_7$—, and which may substituted by $C_1$-$C_{14}$alkyl, hydroxy-$C_1$-$C_{14}$alkyl, hydroxy, —$NR_9R_{10}$ or halogen; or $C_6$-$C_{10}$arylene, which may substituted by $C_1$-$C_{14}$alkyl, hydroxy-$C_1$-$C_{14}$alkyl, hydroxy, amino or halogen;
- $W_1$ is a cationic group; and
- $R_3, R_4, R_5, R_6, R_7, R_8, R_9$ and $R_{10}$ independently from each other are hydrogen; $C_1$-$C_{14}$alkyl; or Z; and
- $An_1^-$, $An_2^-$ and $An_3^-$ independently from each other are an anion with the proviso that 2 radicals represent Z in order to obtain an overall charge of $3^+$.

23. A method according to claims 22, which comprises treating the organic material with said composition and an oxidative agent and, optionally, a further direct dye.

24. A method according to claim 22, which comprises treating the organic material with said composition and at least one single oxidative dye, or treating the organic material with said composition and at least one single oxidative dye and an oxidative agent.

25. A method according to claim 22 wherein the organic material is selected from keratin-containing fibers.

26. A method according to claim 25 wherein the keratin-containing fiber is human hair.

* * * * *